US011642099B2

(12) United States Patent
Weekemp et al.

(10) Patent No.: US 11,642,099 B2
(45) Date of Patent: May 9, 2023

(54) ROLLED FLEXIBLE SUBSTRATE WITH INTEGRATED WINDOW FOR INTRALUMINAL ULTRASOUND

(71) Applicant: KONINKLIJKE PHILIPS N.V., Eindhoven (NL)

(72) Inventors: Johannes Wilhelmus Weekemp, Beek en Donk (NL); Franciscus Johannes Gerardus Hakkens, Eersel (NL); Vincent Adrianus Henneken, Utrecht (NL); Marcus Cornelis Louwerse, Nijmegen (NL); Ronald Dekker, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 58 days.

(21) Appl. No.: 16/768,770

(22) PCT Filed: Nov. 26, 2018

(86) PCT No.: PCT/EP2018/082463
§ 371 (c)(1),
(2) Date: Jun. 1, 2020

(87) PCT Pub. No.: WO2019/110334
PCT Pub. Date: Jun. 13, 2019

(65) Prior Publication Data
US 2021/0169446 A1 Jun. 10, 2021

Related U.S. Application Data

(60) Provisional application No. 62/596,300, filed on Dec. 8, 2017.

(51) Int. Cl.
*A61B 8/12* (2006.01)
*A61B 8/08* (2006.01)
*A61B 8/00* (2006.01)

(52) U.S. Cl.
CPC .............. *A61B 8/12* (2013.01); *A61B 8/0891* (2013.01); *A61B 8/445* (2013.01); *A61B 8/4494* (2013.01)

(58) Field of Classification Search
CPC ......... A61B 8/12; A61B 8/0891; A61B 8/445; A61B 8/4494; B06B 1/0633; H01L 41/27
See application file for complete search history.

(56) References Cited

U.S. PATENT DOCUMENTS

| | | | |
|---|---|---|---|
| 6,283,921 | B1 | 9/2001 | Nix |
| 6,641,540 | B2 | 11/2003 | Fleischman |

(Continued)

FOREIGN PATENT DOCUMENTS

| | | | | |
|---|---|---|---|---|
| WO | 2017167883 | A1 | 10/2017 | |
| WO | WO-2017187756 | A1 * | 11/2017 | ........... A61B 8/4494 |

OTHER PUBLICATIONS

International Search Report & Written Opinion for PCT/EP2018/082463, dated Feb. 28, 2019.

*Primary Examiner* — Sean D Mattson
*Assistant Examiner* — Michael Yiming Fang

(57) ABSTRACT

An intraluminal ultrasound imaging device includes a flexible elongate member configured to be inserted into a body lumen of a patient, the flexible elongate member comprising a proximal portion and a distal portion. The device includes an ultrasound scanner assembly disposed at the distal portion of the flexible elongate member. The ultrasound scanner assembly includes a flexible substrate comprising a longitudinal width extending from an inner edge to an outer edge; a control region embedded in the flexible substrate; a transducer region embedded in the flexible substrate; and a window region disposed between the outer edge of the flexible substrate and the transducer region, and wherein the window region, the transducer region, and the control region (Continued)

are radially arranged relative to one another. Associated devices, systems, and methods are also described.

22 Claims, 21 Drawing Sheets

(56) References Cited

U.S. PATENT DOCUMENTS

| | | | |
|---|---|---|---|
| 6,776,763 B2 | 8/2004 | Nix | |
| 7,226,417 B1* | 6/2007 | Eberle | B06B 1/0633 |
| | | | 29/25.35 |
| 7,846,101 B2 | 12/2010 | Eberle | |
| 9,070,865 B1* | 6/2015 | Snook | H01L 41/0986 |
| 10,668,299 B2 | 6/2020 | Krechting | |
| 2002/0087083 A1* | 7/2002 | Nix | B06B 1/0633 |
| | | | 600/459 |
| 2004/0044286 A1 | 3/2004 | Hossack | |
| 2007/0016071 A1 | 1/2007 | Eberle | |
| 2007/0239024 A1 | 10/2007 | Eberle | |
| 2013/0060141 A1* | 3/2013 | Sinelnikov | A61B 8/4209 |
| | | | 600/439 |
| 2015/0305710 A1 | 10/2015 | Stigall | |
| 2016/0029999 A1 | 2/2016 | Corl | |
| 2016/0228061 A1* | 8/2016 | Kallback | A61B 5/0215 |
| 2019/0069949 A1* | 3/2019 | Vrba | A61B 17/122 |

* cited by examiner

ROLLED FLEXIBLE SUBSTRATE WITH INTEGRATED WINDOW FOR INTRALUMINAL ULTRASOUND

RELATED APPLICATION

This application claims the benefit of and priority to U.S. Provisional Application No. 62/596,300, filed Dec. 8, 2017, which is incorporated by reference in its entirety.

TECHNICAL FIELD

The present disclosure relates generally to intravascular ultrasound (IVUS) imaging and, in particular, to the distal structure of an intravascular imaging device. For example, the distal structure can include a support structure and and/or a flexible substrate that are rolled to facilitate efficient assembly and operation of the intravascular imaging device.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma. Furthermore, because there is no rotating element, the electrical interface is simplified. The solid-state scanner can be wired directly to the imaging system with a simple electrical cable and a standard detachable electrical connector, rather than the complex rotating electrical interface required for a rotational IVUS device.

Manufacturing an intravascular imaging device that can efficiently traverse anatomic structures within the human body is challenging. In that regard, imaging components may create an area of high rigidity and large diameter at the distal portion of the intravascular imaging device, which increase the likelihood of kinking as the intravascular device is steered through anatomical lumens (including, for example but without limitation, small diameter vasculature such as coronary vessels).

Thus, there remains a need for intravascular ultrasound imaging system that overcomes the limitations of a relatively large diameter and rigid imaging assembly to facilitate access to small diameter vasculature and/or other anatomical spaces while maintaining efficient assembly and operation. In particular, there remains a need for new phased array architectures that allow for ease of manufacture while minimizing the overall profile to the imaging portion of the intravascular device (e.g., by reducing the diameter and/or the stiff length).

SUMMARY

Embodiments of the present disclosure provide an improved intravascular ultrasound imaging system for generating images of a blood vessel. A distal portion of an intravascular imaging device can comprise an imaging assembly including a flexible substrate and a support member around which the flexible substrate is wrapped. The flexible substrate can include proximal, distal, and central portions. The imaging assembly may comprise transducer regions and control regions positioned laterally on the central portion of the flexible substrate. When the flexible substrate is rolled or wrapped about the support member, the transducer region is wrapped around or stacked circumferentially atop the control region. Accordingly, the stiff length and overall diameter of the imaging assembly, including the flexible substrate, the transducer region, and the control region, are minimized, thereby facilitating navigation of the intravascular imaging device into small diameter anatomical lumens. The flexible substrate can include an integrally formed support structure that is wrapped/rolled along with the control and transducer regions. The flexible substrate can include an integrally formed imaging window that that is wrapped/rolled along with the control and transducer regions. The sidewalls of the transducer elements can be angled such that the transducer elements are arranged adjacent to one another without colliding when the transducer region is wrapped/rolled.

In an exemplary aspect, an intraluminal ultrasound imaging device is provided. The device includes a flexible elongate member configured to be inserted into a body lumen of a patient, the flexible elongate member comprising a proximal portion and a distal portion; an ultrasound scanner assembly disposed at the distal portion of the flexible elongate member, the ultrasound scanner assembly comprising: a flexible substrate comprising a longitudinal width extending from an inner edge to an outer edge; a control region embedded in the flexible substrate; a transducer region embedded in the flexible substrate; and a window region disposed between the outer edge of the flexible substrate and the transducer region, and wherein the window region, the transducer region, and the control region are radially arranged relative to one another.

In some aspects, the window region comprises an integrated part of the flexible substrate. In some aspects, the window region is disposed adjacent the transducer region and defines the outer edge of the flexible substrate. In some aspects, the window region includes a variable thickness from an inner window edge to an outer window edge. In some aspects, the thickness of the window region is greatest in an area overlying the transducer region when the flexible substrate is in a rolled configuration. In some aspects, flexible substrate includes a central axis extending through a longitudinal width of the flexible substrate, and the window region, the transducer region, and the control region are stacked adjacent one another along the central axis. In some aspects, the window region, the transducer region, and the control region are coaxially aligned along the central axis. In some aspects, the flexible substrate is rolled into a layered, annular scanner assembly with the control region forming an inner layer, the transducer region forming a middle layer, and the window region forming an outer layer of the scanner assembly. In some aspects, the flexible substrate further comprises a support region disposed between the inner edge of the flexible substrate and the control region, wherein the window region, the transducer region, the control region, and the support region are laterally disposed adjacent one another. In some aspects, the flexible substrate is rolled into a layered, annular scanner assembly with the support region forming an innermost first layer defining a cylindrical lumen, the control region forming a second middle layer, the transducer region forming a third middle layer, and the window region forming an outermost layer of the scanner assembly. In some aspects, the window region comprises a flange extending from the outer edge of the flexible substrate. In some aspects, the flexible substrate further comprises a transition region disposed between the window region and the transducer region. In some aspects, the transition region is sized and configured to enable the rolling of the transducer region and the window region of flexible substrate into separate, nested cylinders.

In an exemplary aspect, a method of assembling an intraluminal ultrasound imaging device. The method includes obtaining a flexible substrate comprising a central axis extending along the width of the flexible substrate from an inner edge to an outer edge; positioning an ultrasound transducer region, a control region, and a window region laterally along the central axis of the flexible substrate, wherein the window region is disposed between the outer edge and the ultrasound transducer region; and rolling the flexible substrate into a layered cylindrical shape, wherein the control region forms an inner layer, the ultrasound transducer region forms a middle layer, and the window region forms an outer layer.

In some aspects, the method further includes obtaining a support member comprising a lumen running therethrough. In some aspects, the method further includes positioning the support member adjacent the control region before rolling the flexible substrate. In some aspects, rolling the flexible substrate into a layered cylindrical shape comprises wrapping the control region around the support member, wherein the control region forms an inner layer surrounding the support member, the ultrasound transducer region forms a middle layer surrounding the control region, and the window region forms an outer layer surrounding the ultrasound transducer region. In some aspects, the window region is radially spaced from the ultrasound transducer region, the ultrasound transducer region is radially spaced from the control region, and the control region is radially spaced from the support member. In some aspects, the window region is radially spaced from the ultrasound transducer region and the ultrasound transducer region is radially spaced from the control region. In some aspects, the method further includes inserting acoustic matching medium between the window region and the ultrasound transducer region.

In some aspects, the flexible substrate further comprises a transition region disposed between the transducer region and the window region. In some aspects, the window region has a generally rectangular shape. In some aspects, the control region is disposed adjacent the inner edge of the flexible substrate. In some aspects, the transducer region comprises a plurality of transducers, and the control region comprises a plurality of controllers. In some aspects, the plurality of transducers comprises a plurality of capacitive micromachined ultrasound transducers.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 13 is a diagrammatic perspective view of the scanner assembly, FIG. 14 is a side view of the scanner assembly, and FIG. 15 is an oblique view of the scanner assembly.

FIG. 16 is a diagrammatic perspective view of the scanner assembly, FIG. 17 is a side view of the scanner assembly, and FIG. 18 is an oblique view of the scanner assembly.

FIG. 19 is a diagrammatic perspective view of the scanner assembly and FIG. 20 is a diagrammatic front view of a distal portion of the scanner assembly.

FIG. 21 is a diagrammatic side view of the exemplary transducers with the flexible substrate in a flat configuration, and FIG. 22 is a diagrammatic side view of the exemplary transducers with the flexible substrate in a curved (or rolled) configuration.

FIG. 24a is a diagrammatic top view the scanner assembly, and FIG. 24b is a diagrammatic front view of a distal portion of the scanner assembly.

DETAILED DESCRIPTION

Figure 1:
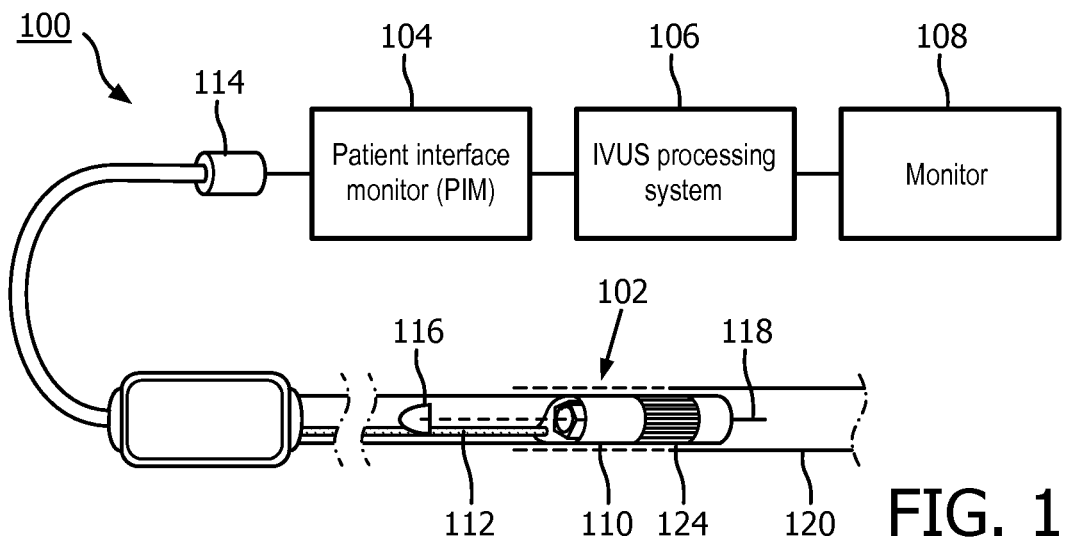
FIG. 1 is a diagrammatic schematic view of an imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the focusing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a diagrammatic schematic view of an intravascular ultrasound (IVUS) imaging system 100, according to aspects of the present disclosure. The IVUS imaging system 100 may include a solid-state IVUS device 102 such as a catheter, guide wire, or guide catheter, a patient interface module (PIM) 104, an IVUS processing system or console 106, and a monitor 108.

At a high level, the IVUS device 102 emits ultrasonic energy from a transducer array 124 included in scanner assembly 110 mounted near a distal end of the catheter device. The ultrasonic energy is reflected by tissue structures in the medium, such as a vessel 120, surrounding the scanner assembly 110, and the ultrasound echo signals are received by the transducer array 124. The PIM 104 transfers the received echo signals to the console or computer 106 where the ultrasound image (including the flow information) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A, 206B, illustrated in FIG. 2, included in the scanner assembly 110 to select the particular transducer array element(s) to be used for transmit and receive, (2) providing the transmit trigger signals to the integrated circuit controller chip(s) 206A, 206B included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 206A, B of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. Generally, the system 100 and/or the device 102 can be used in any suitable lumen of a patient body. In that regard, the system 100 can be an intraluminal ultrasound imaging system 100, and the device 102 can be an intraluminal ultrasound imaging system 100. The system 100 and/or the device 102 can be referenced as an interventional device, a therapeutic device, a diagnostic device, etc. The device 102 can be sized and shaped, structurally arranged, and/or otherwise configured to be positioned within the vessel or lumen 120. Lumen or vessel 120 may represent fluid filled or surrounded structures, both natural and man-made. The lumen or vessel 120 may be within a body of a patient. The vessel 120 may be a blood vessel, such as an artery or a vein of a patient's vascular system, including cardiac vasculature, peripheral vasculature, neural vasculature, renal vasculature, and/or or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be may be used to examine man-made structures such as, but without limitation, heart valves, stents, shunts, filters and other devices.

Figure 2:
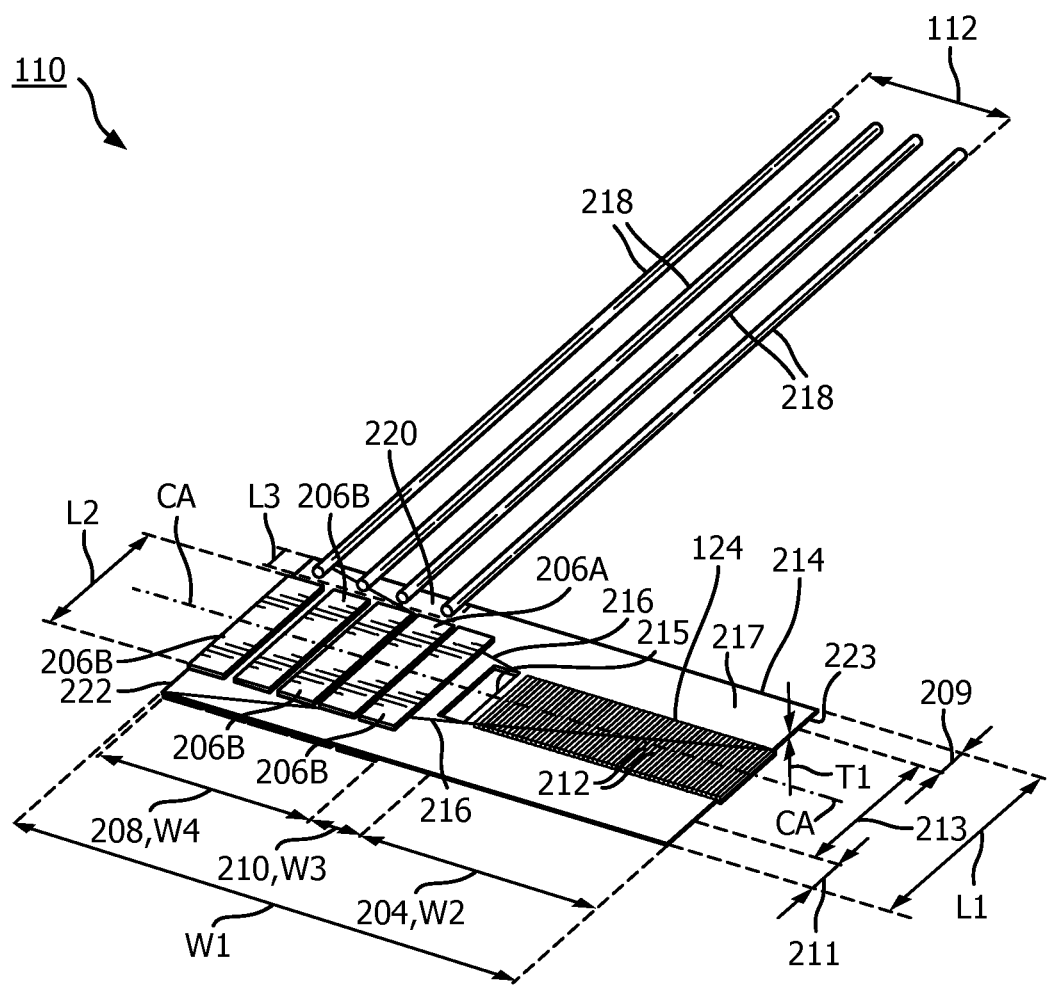
FIG. 2 is a diagrammatic perspective view of the top of a scanner assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include one conductor or a plurality of conductors, including two, three, four, five, six, seven, or more conductors 218 (as shown in FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

Figure 3:
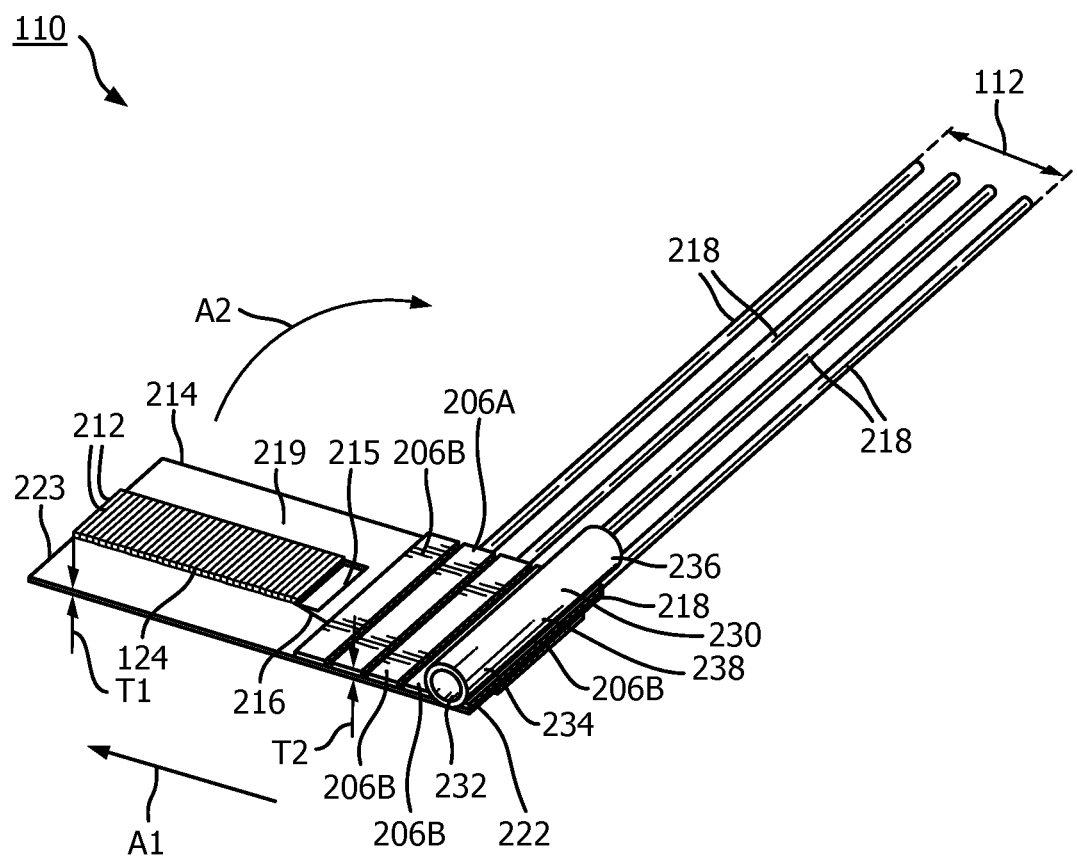
FIG. 3 is a diagrammatic perspective view of the bottom of the scanner assembly shown in FIG. 2 in a flat configuration, according to aspects of the present disclosure.

FIG. 2 is a perspective view of the top of an ultrasound scanner assembly 110 in an unrolled or flat configuration according to an embodiment of the present disclosure. FIG. 3 is a perspective view of the bottom of the scanner assembly 110 shown in FIG. 2 in a flat configuration and a support member 230, according to aspects of the present disclosure. In particular, FIG. 3 illustrates the flexible substrate 214 and the support member 230 prior to the flexible substrate 214 being rolled around the support member 230.

The assembly 110 includes a transducer array 124 formed in a transducer region 204 and transducer control logic dies 206 (including dies 206A and 206B) formed in a control region 208, with a transition region 210 disposed therebetween. The transducer array 202 is a non-limiting example of a medical sensor element and/or a medical sensor element array. The transducer control logic dies 206 is a non-limiting example of a controller or a control circuit.

The transducer control logic dies 206 and the transducers 212 are mounted on a flexible substrate 214 (or flex circuit 214) that is shown in an unrolled or flat configuration in FIG. 2. The flexible substrate 214 includes three zones or portions extending along an overall longitudinal length L1: a proximal portion 209, a distal portion 211, and a central portion 213. In the embodiment shown in FIG. 2, the transducer region 204, the transition region 210, and the control region 208 are laterally disposed (or stacked) adjacent one another within the central portion 213. Thus, the transducers 212 are positioned laterally (or stacked) relative to the transducer control logic dies 206 within the central portion 213 of the flexible substrate 214. The term "adjacent" as used herein does not necessitate that the transducer region 204 and the control region are in contact with each other. The term "adjacent" is used to mean simply that the two regions are generally positioned in a coaxial fashion. In other embodiments, the transducers 212 and/or the transducer control logic dies 206 may be disposed at least partially within the proximal portion 209 and/or the distal portion 211. As the names imply, the transducer region 204 contains the transducers 212, and the control region 208 contains the transducer control logic dies 206. This lateral arrangement of the transducers 212 and the transducer control logic dies 206, where the transducer region 204 and the control region 208 are positioned side-by-side along a longitudinal width W1 of the flexible substrate, minimizes the overall longitudinal length L1 and an overall stiff length L2 of the scanner assembly 110. In this embodiment, the stiff length L2 of the scanner assembly 110 comprises the length of the longer of the two stiff components included on the flexible substrate 214, which in this case is the length of the transducer control logic dies 206. In contrast, for example, positioning the transducers 212 distal to the transducer control logic dies 206 on the flexible substrate 214 would necessarily require an increase in both the overall length L1 of the flexible substrate 214 and the stiff length L2 of the scanner assembly 110 (namely, the combined lengths of the transducer control logic dies 206, the transition region 110, and the transducers 212). The length L1 may measure between 0.5 mm and 5 mm, including values between 0.5 mm and 1.5 mm, such as 0.5 mm, 1 mm, 1.5 mm, 2 mm, and/or other suitable values both larger and smaller. The length L2 may measure between 0.5 mm and 5 mm, or between 1 mm and 5 mm, including values such as a 0.5 mm, 1 mm, 1.5 and/or other suitable values both larger and smaller.

In the pictured embodiment, both the transducer region 204 and the control region 208 are aligned along a central axis CA extending through the central portion 213 from an inner edge 222 to an outer edge 223 of the flexible substrate 214. Although the transducers 212 and the transducer control logic dies 206 are shown as coaxially aligned along the central axis CA in the pictured embodiment in FIG. 2, the transducers 212 and the transducer control logic dies 206 may be disposed upon flexible substrate 214 in dissimilar, unaligned patterns in other embodiments. The transducer region 204 is disposed adjacent the outer edge 223 of the flexible substrate 214. The control region 208 is disposed adjacent the inner edge 222 of the flexible substrate 214. In some embodiments, the transducer region 204 and/or the control region 208 may be spaced apart from the outer edge 223 and the inner edge 222, respectively, of the flexible substrate 214. The transition region 210 is disposed between the control region 208 and the transducer region 204. The dimensions of the transducer region 204, the control region 208, and the transition region 210 (e.g., widths W2, W3, and W4, respectively) can vary in different embodiments. In various embodiments, the widths W2, W3, and W4 can be substantially similar or dissimilar. For example, in the pictured embodiment, the width W3 of the transition region 210 is substantially smaller than the widths W2 and W4 of the transducer region 204 and the control region 208, respectively. The width W2 of the transducer region 204 and/or the width W3 of the control region 208 can be between approximately 1 and 5 mm, for example. The width W4 of the transition region 210 can be any suitable value, including between approximately 1 and 5 mm. The width W2 of the transducer region 204 and/or the width W3 of the control region 208 can be between approximately 1 and 5 mm, and/or other suitable values both larger and smaller, for example. The width W4 of the transition region 210 can be any suitable value, including between approximately 1 and 5 mm and/or other suitable values both larger and smaller, for example.

The transducer array 124 may include any number and type of ultrasound transducers 212, although for clarity only a limited number of ultrasound transducers are illustrated in FIG. 2. In the pictured embodiment, the transducer array 124 includes 40 individual ultrasound transducers 212. In a further embodiment, the transducer array 124 includes 64 ultrasound transducers 212. In a further embodiment, the transducer array 124 includes 32 ultrasound transducers 212. Other numbers, both larger and smaller, are both contemplated and provided for. With respect to the types of transducers, in some embodiments, the ultrasound transducers 212 are capacitive micromachined ultrasound transducers (cMUTs), for example as disclosed in U.S. application Ser. No. 14/812,792, filed Jul. 29, 2015, and titled "Intravascular Ultrasound Imaging Apparatus, Interface Architecture, and Method of Manufacturing," which is hereby incorporated by reference in its entirety. Incorporating cMUTs minimize the overall profile and diameter of the scanner assembly 110 because cMUTs are significantly smaller and thinner than several other types of transducers. Moreover, incorporating cMUTs may advantageously increase the ease of assembly by allowing the flexible substrate to be efficiently made atop the silicon wafer on which cMUTs and their conductive traces are already created. In addition, the definition of more precise transducer islands of the cMUT fabrication process and the slim, flexible nature of the silicon wafer may decrease the amount or degree of dicing of the flexible substrate 214 to enable adequate curvature of the scanner assembly 110. In other embodiments, the ultrasound transducers 212 can be piezoelectric micromachined ultrasound transducers (PMUTs) fabricated on a microelectromechanical system (MEMS) substrate using a polymer piezoelectric material, for example as disclosed in U.S. Pat. No. 6,641,540, which is hereby incorporated by reference in its entirety. In alternate embodiments, the transducer array includes piezoelectric zirconate transducers (PZT) transducers such as bulk PZT transducers, single crystal piezoelectric materials, other suitable ultrasound transmitters and receivers, and/or combinations thereof.

The scanner assembly 110 may include various transducer control logic, which in the illustrated embodiment is divided into discrete control logic dies 206. In various examples, the control logic of the scanner assembly 110 performs: decoding control signals sent by the PIM 104 across the cable 112, driving one or more transducers 212 to emit an ultrasonic signal, selecting one or more transducers 212 to receive a reflected echo of the ultrasonic signal, amplifying a signal representing the received echo, and/or transmitting the signal to the PIM across the cable 112. In the illustrated embodiment, a scanner assembly 110 having 40 ultrasound transducers 212 divides the control logic across five control logic dies 206. Designs incorporating other numbers of control logic dies 206, including 8, 9, 16, 17 and more, are utilized in other embodiments. In general, the control logic dies 206 are characterized by the number of transducers they are capable of driving, and an exemplary control logic dies 206 drive 4, 8, and/or 16 transducers.

The control logic dies are not necessarily homogenous. In some embodiments, a single controller is designated a master control logic die 206A and contains the communication interface for the cable 112 (i.e., the conductors 218). Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a transducer 212 to emit an ultrasonic signal and selects a transducer 212 to receive an echo. In some embodiments, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and four slave controllers 206B are provided with ten transducers assigned to each slave controller 206B.

The flexible substrate 214, on which the transducer control logic dies 206 and the transducers 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, other flexible printed semiconductor substrates as well as products such as Upilex® (registered trademark of Ube Industries) and TEFLON® (registered trademark of E.I. du Pont). In the flat configuration illustrated in FIGS. 2 and 3, the flexible substrate 214 has a generally rectangular shape. Although the flexible substrate 214 is shown herein as having a generally rectangular shape, other embodiments may include a flexible substrate 214 having alternative shapes (e.g., square). In some instances, the flexible substrate 214 further comprises metallic interconnection circuitry formed from a malleable metal (such as gold) deposited by means of known sputtering, plating and etching techniques employed in the fabrication of microelectronic circuits upon a chromium adhesion layer on a surface of the flexible substrate 214.

Figure 4:
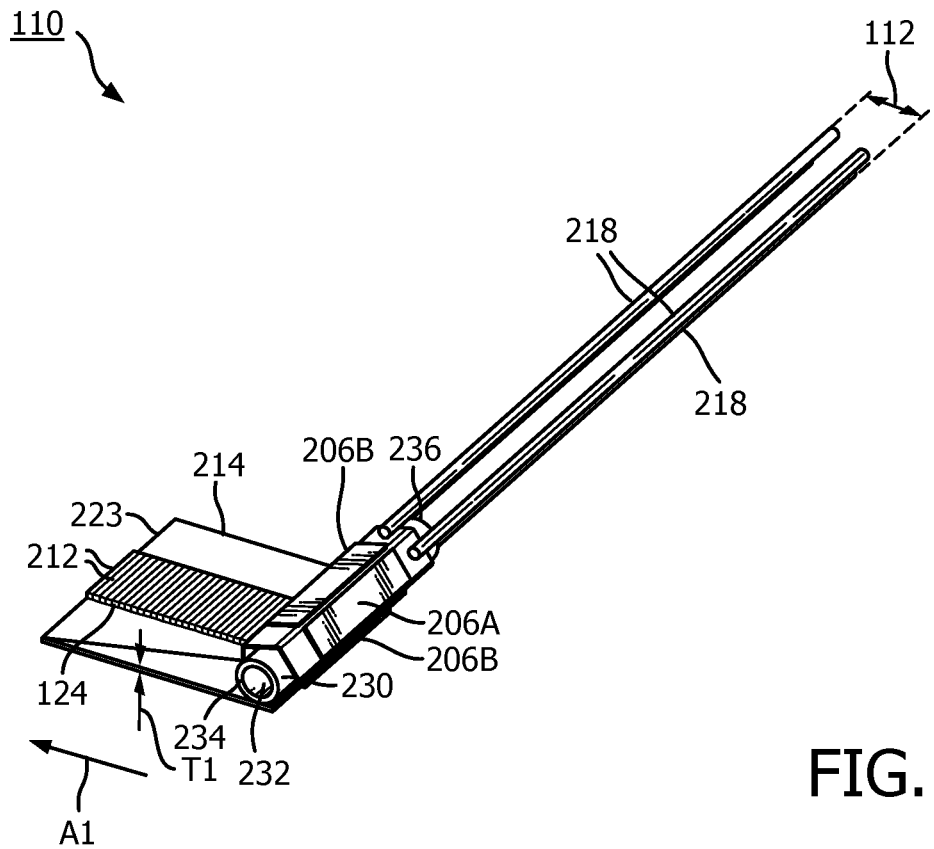
FIG. 4 is a diagrammatic perspective view of a scanner assembly shown in FIG. 2 in a partially rolled configuration around a support member, according to aspects of the present disclosure.
Figure 5:
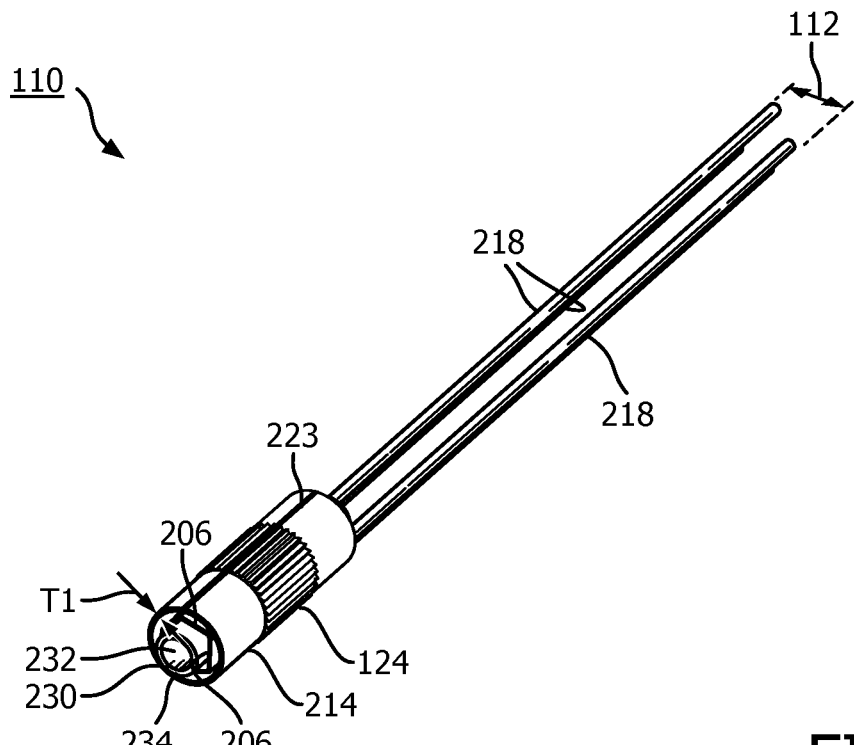
FIG. 5 is a diagrammatic perspective view of a scanner assembly shown in FIG. 2 in a rolled configuration around the support member shown in FIG. 4, according to aspects of the present disclosure.
Figure 6:
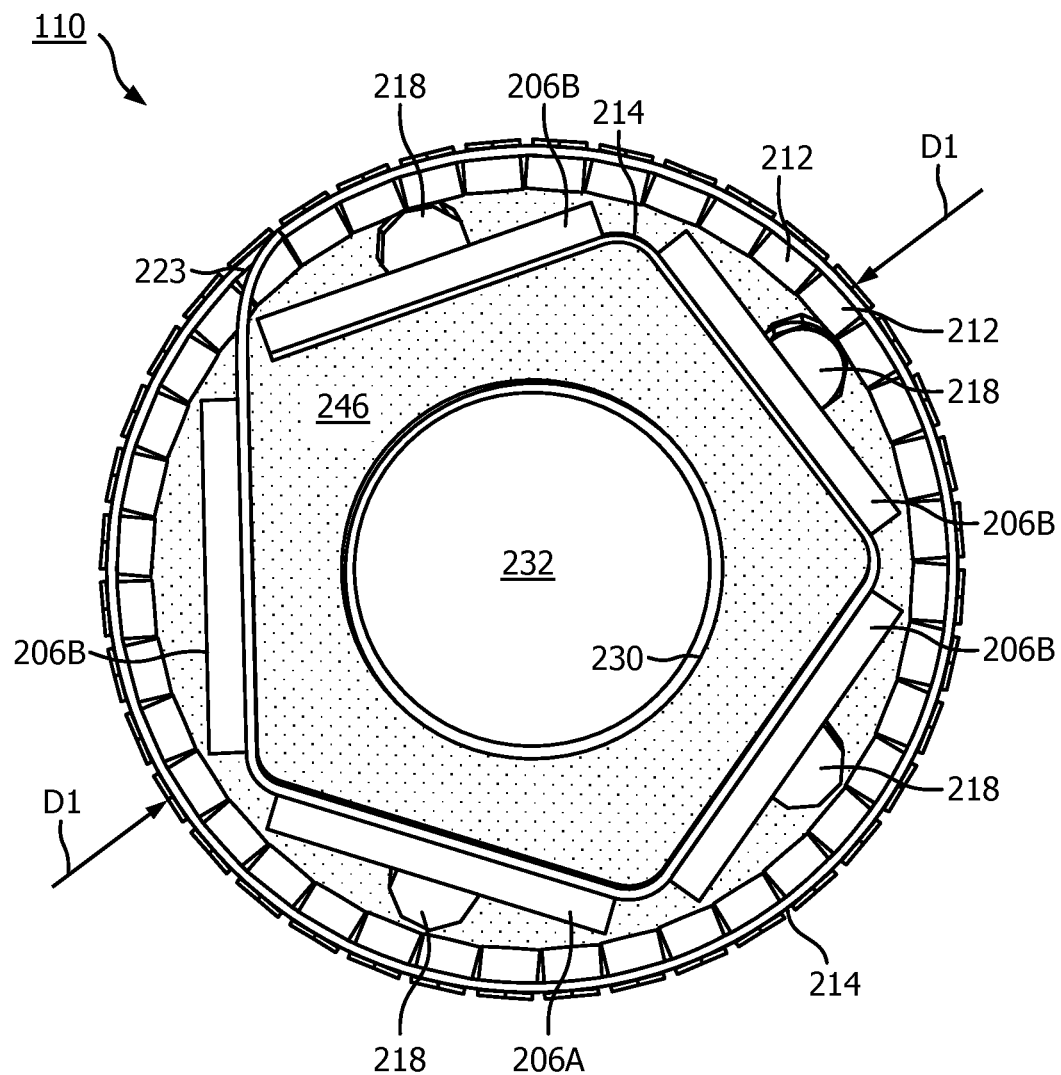
FIG. 6 is a diagrammatic front view of a distal portion of the scanner assembly, including the flexible substrate and the support member, according to aspects of the present disclosure.

The transition region 210 can be non-rectangular and may include one or more cutouts or slots that increase the flexibility of the flexible substrate 214 and/or enable the separate regions of the flexible substrate to partially nest within each other to more easily assume a rolled configuration with a reduced profile. In the pictured embodiment, the flexible substrate 214 includes a slot 215 disposed within the transition region 210. The slot 215 comprises a sacrificial area that may be removed from the flexible substrate 214 by any of a variety of fabrication processes known to one of skill in the art, including without limitation, chemical etching, laser etching, mechanical sawing, and/or other suitable etching/removal process. In the pictured embodiment, the slot 215 is spaced slightly from the control region and is adjacent the transducer array 124. Conductive traces 216 connect the transducer array 124, the transducer control logic dies 206, and the transmission line bundle or cable 112 (i.e., the conductors 218). The slot 215 may extend through the flex circuit from a first surface 217 of the flexible substrate 214 to an opposite second surface 219, as shown in FIGS. 2 and 3, or may be an indentation within the second surface 219. The slot 215 is shaped and configured to facilitate the wrapping or rolling the flexible substrate 214 into a generally cylindrical shape, as shown in FIGS. 4 and 5, such that the transducer region 204 forms a complete cylinder (as shown in FIG. 6).

As shown and described herein, the flexible substrate 214 is configured to be wrapped around a support member 230 (as shown in FIG. 3) to form a cylindrical toroid in some instances. Therefore, the thickness T1 of the film layer of the flexible substrate 214 is generally related to the degree of curvature in the final assembled scanner assembly 110. The thickness T1 extends from the first surface 217 of the flexible substrate 214 to the second surface 219 of the flexible substrate 214. In some embodiments, the thickness of the film layer is between 2 μm and 10 μm. In some instances, the thickness T1 of the flexible substrate 214 is twice as thin as the flex circuit of the EagleEye® catheter available from Volcano Corporation, thereby allowing for a smaller bending radius and more "rolls" or layers of the flexible substrate 214 to wrap around the support member 230 (shown in FIG. 3). In the pictured embodiment, the flexible substrate 214 includes embedded tracks on which both the ultrasound transducers 212 and the control logic dies 206 are mounted, thereby facilitating a thin profile and reduced overall thickness T2 of the scanner assembly 110 in the flat configuration. Having embedded tracks for the transducers 212 and the control logic dies 206 enables rolling of the flexible substrate 214 (and overall scanner assembly 110) into a desirable form (e.g., a cylindrical form) with an optimally small diameter, as shown in FIG. 5. Such embedded tracks may be formed in the flexible substrate 214 by any of a variety of fabrication processes known to one of skill in the art. These embedded tracks are in the range of 0.5 to 1 micron and do not substantively add to the overall diameter.

In some embodiments, to electrically interconnect the control logic dies 206 and the transducers 212, the flexible substrate 214 further includes conductive traces 216 formed on the film layer. The conductive traces 216 couple and carry signals between the control logic dies 206 and the transducers 212. In particular, the conductive traces 216 providing communication between the control logic dies 206 and the transducers 212 extend along the flexible substrate 214 across the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 0.5 and 1.5 μm. For example, in an embodiment, 20 μm wide conductive traces 216 are separated by 20 μm of space. In some embodiments, the width of the traces can be as small as 3 microns with spaces of 3 microns. The width of a conductive trace 216 on the flexible substrate 214 may be further determined by the width of the conductor 218 to be coupled to the trace/pad. This selected magnitude for the thickness, the width, and separation of the conductive traces 216 enables the conductive traces 216 to be sufficiently conductive while maintaining relative flexibility and resiliency so that the conductor lines do not break or malfunction after rolling the flexible substrate 214 into the cylindrical shape shown in FIGS. 4 and 5. The conductive traces 216 within the flexible substrate also lend a measure of structure and stiffness to the flexible substrate 214. In some instances, the combination of the flexible substrate 214 and the conductive traces 216 is referred to as a flex circuit 214. Although the flexible substrate 214 may occasionally described herein as a flex circuit, it is understood that the transducers and/or controllers may be arranged to form the imaging assembly 110 in other configurations, including those omitting a flex circuit.

The flexible substrate 214 includes a conductor interface 220 (shown by dotted lines in FIG. 2) in the pictured embodiment. The conductor interface 220 defines the portion of the flexible substrate 214 where the conductors 218 of the transmission line bundle 112 are coupled to the flexible substrate 214. For example, the bare conductors 218 of the transmission line bundle 112 are electrically coupled to the flexible substrate 214 at the conductor interface 220. The conductor interface 220 is positioned in the proximal portion of the flexible substrate 214. In some embodiments, the conductor interface 220 can be a tab or flange extending proximally from the main body of flexible substrate 214. In that regard, the main body of the flexible substrate 214 can refer collectively to the transducer region 204, controller region 208, and the transition region 210. In the illustrated embodiment, the conductor interface 220 is positioned adjacent the inner edge 222 and the control region 208 of the flexible substrate 214. In other embodiments, the conductor interface 220 may be positioned adjacent other parts of the flexible substrate 214, such as the outer edge 223, the transition region 210, or the transducer region 204. In other embodiments, the flexible substrate 214 lacks the conductor interface 220. A value of a dimension of the tab or conductor interface 220, such as a length L3, can be less than the value of a dimension of the main body of the flexible substrate 214, such as the length L1. The length L1 includes the lengths of the proximal portion 209, the central portion 213, and the distal portion 211 of the flexible circuit 214.

In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, and/or other suitable materials. As described in greater detail herein, the support member 230, the flexible substrate 214, the conductor interface 220 and/or the conductor(s) 218 can be variously configured to facilitate efficient manufacturing and operation of the scanner assembly 110.

According to the illustrated embodiments herein, the scanner assembly 110 is transitioned from a flat configuration (as shown in FIGS. 2 and 3) to a rolled, generally cylindrical configuration (as shown in FIG. 5). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND TRANSDUCER ASSEMBLY HAVING A FLEXIBLE SUBSTRATE," each of which is hereby incorporated by reference in its entirety.

FIGS. 4 and 5 are diagrammatic perspective views of the scanner assembly 110 shown in FIGS. 2 and 3 in a rolled configuration around the support member 230, according to aspects of the present disclosure. In particular, FIG. 4 illustrates the scanner assembly 110 in a partially rolled configuration around the support member 230, and FIG. 5 illustrates the scanner assembly 110 in a completely rolled configuration around the support member 230.

In the pictured embodiment, the support member 230 comprises a cylindrical tube having a lumen 232 extending therethrough. The support member 230 has a distal end 234 and a proximal end 236. The support member 230 can be referenced as a unibody in some instances. The support member 230 can be composed of a metallic material, such as stainless steel, or non-metallic material, such as a plastic or polymer as described in U.S. Provisional Application No. 61/985,220, "Pre-Doped Solid Substrate for Intravascular Devices," filed Apr. 28, 2014, the entirety of which is hereby incorporated by reference herein. The lumen 232 is in communication with the exit port 116 and is sized and shaped to receive the guide wire 118 (shown in FIG. 1). The lumen 232 can be sized and shaped to accommodate a flexible, inner, proximal member and/or a guide wire.

The support member 230 can be manufactured accordingly to any suitable process. For example, the support member 230 can be machined, such as by removing material from a blank to shape the support member 230, or molded, such as by an injection molding process. In some embodiments, the support member 230 may be integrally formed as a unitary structure, while in other embodiments the support member 230 may be formed of different components, such as a ferrule (i.e., a cylindrical body or ring) and stands (e.g., at the distal end 234 and a proximal end 236 of the support member 230) that are fixedly coupled to one another. Although not shown in FIGS. 2-5, the proximal portion 236 and distal portion 234 of the support member 230 may be shaped and configured to elevate and support the proximal portion 209 and the distal portion 211 of the flexible substrate 214. In that regard, portions of the flexible substrate 214, such as the transducer portion 204 and the control portion 208, can be spaced from a central body portion 238 (shown in FIG. 3) of the support member 230 extending between the proximal end 236 and distal end 234 of the support member 230.

The support member 230 can be substantially cylindrical in some embodiments. Other shapes of the support member 230 are also contemplated including geometrical, non-geometrical, symmetrical, non-symmetrical, cross-sectional profiles. Different portions the support member 230 can be variously shaped in other embodiments. The support member 230 can be shaped to compliment the optimal orientation of the flexible substrate 214 around the support member 230. The proximal end 236 and distal end 234 of the support member 230 can have the same outer diameter or different outer diameters. For example, the support member may have a tapered profile where the distal end 234 has a larger or smaller outer diameter than the proximal end 236. In one embodiment, the proximal end 236 may have a larger outer diameter than the outer diameters of the distal end 234 or the central body portion 238 extending between the distal and proximal end 234, 236. In some embodiments, an inner diameter of the support member 230 (e.g., the diameter of the lumen 232) can correspondingly increase or decrease as the outer diameter changes. In other embodiments, the inner diameter of the support member 230 remains the same despite variations in the outer diameter. The support member 230 may be sized and shaped to allow greater flexibility for the intravascular device. For example, the support member 230 may compliment the size and shape the rolled flexible substrate 214. The dimensions of the support member 230 can be selected such that the intravascular device 102 has a diameter between approximately 2 Fr and approximately 10 Fr, for example.

As shown in FIG. 3, before commencement of the rolling process, the support member 230 is positioned atop the control region 208 on the second surface 219 of flexible substrate 214. In particular, the support member 230 is positioned adjacent the inner edge 222 of the flexible substrate 214. The support member 230 is positioned such that the distal portion 211 of the flexible substrate 214 is adjacent the distal end 234 of the support member 230 and the proximal portion 209 of the flexible substrate 214 is adjacent the proximal end 236 of the support member 230. In some embodiments, one or more adhesives can be disposed between various components at the distal portion of the intravascular device 102. For example, the flexible substrate 214 and the support member 230 may be coupled to one another via an adhesive prior to the rolling process. After the support member 230 is appropriately positioned, the rolling process begins by rolling the support member 230 and the flexible substrate 214 simultaneously in the direction of the arrow A1. Alternatively or additionally, the flexible substrate 214 may be wrapped around the stationary support member 230 in the direction of arrow A2. After the rolling process or wrapping process is concluded, as shown in the cross-sectional view illustrated in FIG. 6, the scanner assembly 110 resembles a multilayered cylindrical structure with stacked imaging components, with the support member 230 forming an inner layer, the control region 208 forming a middle layer, and the transducer region 204 forming an outer layer of the scanner assembly 110.

FIG. 6 is a diagrammatic front view of a distal portion of the scanner assembly 110 in a completely rolled configuration around the support member 230, according to aspects of the present disclosure. The scanner assembly 110 will generally be positioned at a distal portion of the IVUS device 102, as shown in FIG. 1. The generally cylindrical shape shown in FIGS. 5 and 6 is obtained by wrapping or rolling the flat flexible substrate 214 and embedded imaging components shown in FIG. 2 around the support member 230 into an annular, stacked structure by means of the rolling or wrapping process described above with reference to FIGS. 3-5. The flexible substrate 214 is typically formed into a very small cylindrical shape in order to accommodate the space limitations of blood vessels. In such instances, the range of diameters for cylindrically shaped ultrasound transducer assemblies is typically within the range of 0.5 mm to 3.0 mm. However, it is contemplated that an overall diameter D1 of the cylindrical, stacked scanner assembly 110 in the IVUS device 102 may be on the order of 0.8 mm. to 1.2 mm. In some embodiments, the slim profile and flexible nature of the cMUT transducers on the flexible substrate 214 allow for a decrease in the overall diameter of the distal end of the IVUS imaging device 102 and a decrease in the overall stiff length of the scanner assembly 110. The thinner profiles of each of the layered components (i.e., the control region 208 and the transducer region 204) allow for a slimmer overall profile and reduced overall diameter of the scanner assembly 110. Moreover, the laterally stacked imaging components (i.e., the control region 208 and the transducer region 204) on the flexible substrate 214 allow for a decrease in the overall stiff length of the scanner assembly 110. Both of these features of the scanner assembly 110 can advantageously increase the flexibility of the IVUS device 102 and decrease the likelihood of kinking while the intravascular device is maneuvered through a patient's anatomy (e.g., including the coronary vasculature).

To improve acoustic performance, any cavities between the flexible substrate 214 and the surface of the support member 230 are generally filled with a backing material 246. The liquid backing material 246 has a relatively low acoustic impedance, and can be introduced between the flexible substrate 214 and the support member 230 via passageways in the support member 230 (not shown). The backing material 246 fills the space between the support member 230 and the transducer array 124 as well as the gaps between adjacent individual transducers 212. The backing material 246 possesses the ability to highly attenuate the ultrasound which is transmitted by the transducer array 124. The backing material 246 also provides support for the transducer elements. The backing material 246 can be cured to allow it to solidify and set in a sufficiently short period of time to meet manufacturing needs. A number of known materials meeting the above described criteria for a good backing material will be known to those skilled in the art. An example of such a backing material comprises a mixture of epoxy, hardener and phenolic microballoons providing high ultrasound signal attenuation and satisfactory support for the ultrasound transducer assembly.

Figure 7:
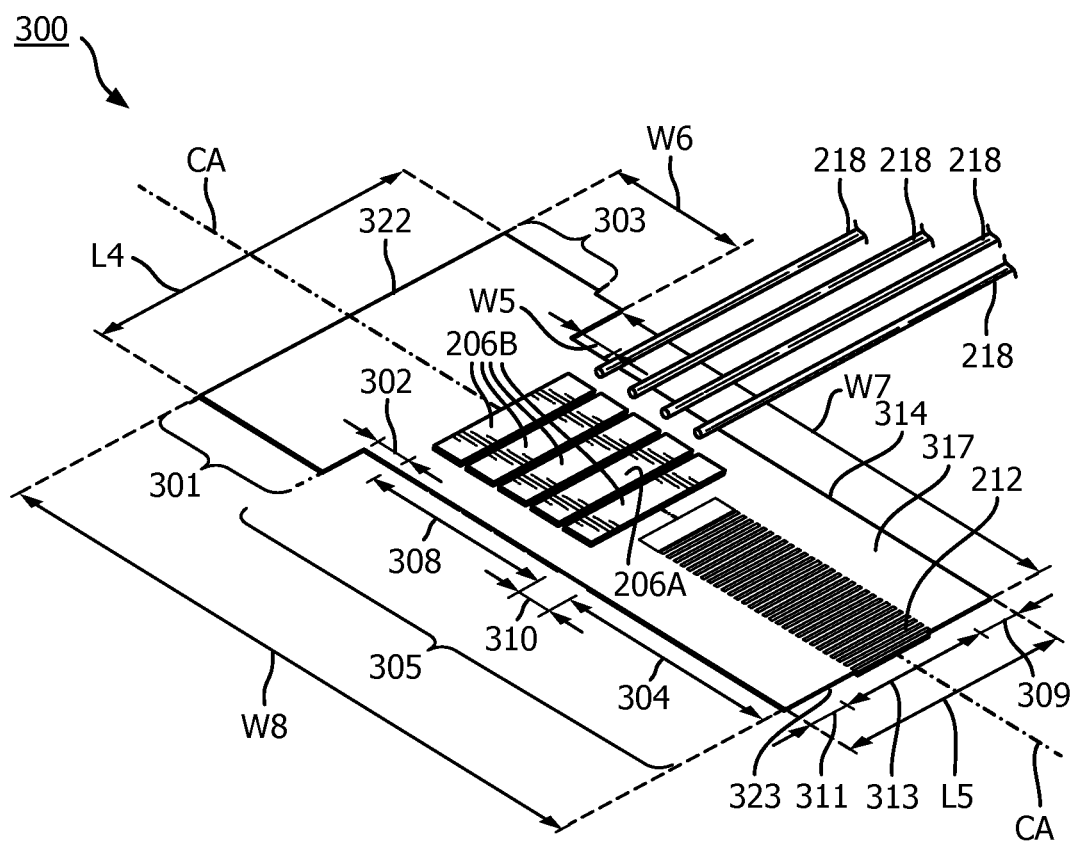
FIG. 7 is a diagrammatic perspective view of the top of another exemplary scanner assembly in a flat configuration, according to aspects of the present disclosure.
Figure 8:
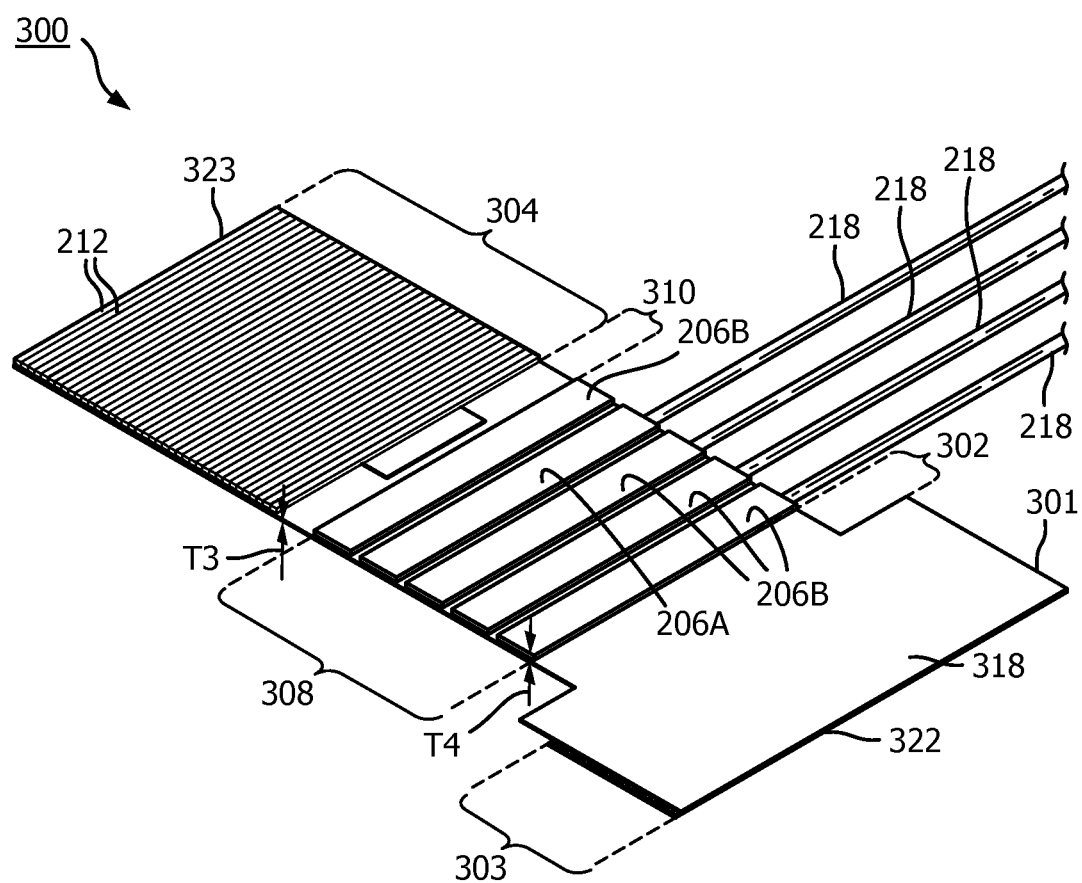
FIG. 8 is a diagrammatic perspective view of the bottom of the scanner assembly shown in FIG. 7 in a flat configuration, according to aspects of the present disclosure.

FIGS. 7 and 8 illustrate the scanner assembly 300, which includes several components that are substantially similar in form and function to the scanner assembly 110 described above with respect to FIGS. 2-6. In particular, FIG. 7 is a perspective view of the top of an ultrasound scanner assembly 300 in an unrolled or flat configuration, according to an embodiment of the present disclosure. FIG. 8 is a perspective view of the bottom of the scanner assembly 300 shown in FIG. 7 in a flat configuration.

The scanner assembly 300 comprises a flexible substrate 314 and several embedded imaging components. The flexible substrate 314 is substantially similar to the flexible substrate 214 except for the differences described herein. FIG. 7 illustrates a flexible substrate 314 prior to the flexible substrate 314 being rolled into a cylindrical shape. In particular, unlike the flexible substrate 214, the flexible substrate 314 comprises a support region 301 and a second transition region 302 in addition to a transducer region 304, a control region 308, and a first transition region 310. The support region 301 comprises a tab or flange extending from a main body 305 of the flexible substrate 314. The main body 305 comprises the portion of the flexible substrate 314 that includes the second transition region 302, the control region 308, the first transition region 310, and the transducer region 304. In the pictured embodiment, the second transition region 302 is part of the main body 305 and lies between the control region 308 and the support region 301. In FIG. 7, the second transition region 302 has relatively a same length L5 as the main body of the flexible substrate 314. In other embodiments, the second transition region 302 may be sized differently than the main body 305 of the flexible substrate 314. The second transition region 302 includes a width W5 that facilitates the rolling of the flexible substrate 314 into separate, nested cylinders, where each cylinder is formed from one of the support region 303, the control region 208, and the transducer region 304. The width W5 of the transition region 310 can be any suitable value, including between approximately 5 and 15 mm. The support region 301 defines an inner edge 322 of the flexible substrate 314, and the transducer region 304 defines the outer edge 323 of the flexible substrate 314. The support region 301, the second transition region 302, the control region 308, the first transition region 310, and the transducer region 304 are all arranged laterally and adjacent to one another along a central axis running along a width W8 of the entire flexible substrate 314. This has the advantage of reducing an overall longitudinal length L4 of the scanner assembly 300.

The support region 301 includes a plurality of parallel elongated wires 303 that are embedded into the flexible substrate 314. In the pictured embodiment, the wires 303 extend the length L4 of the flexible substrate 314. In some embodiments, the wires 303 may measure less or greater in length than the overall longitudinal length L4 of the entire flexible substrate 314. The support region 301 includes a width W6 that measures less than the width W7 of the main body 305 of the flexible substrate 314. The wires 303 may be formed of any of a variety of rigid elements, including without limitation, embedded tracks and/or metal wires, configured to create a reinforced lumen when the support region 301 is rolled into a cylindrical shape. In some embodiments, the wires 303 may be 15 micron Tungsten wires. Different dimensions for the wires 303 are contemplated.

As shown in FIG. 8, the flexible substrate 314 has a thickness T3 extending from a first surface 317 (shown in FIG. 8) to a second, opposite surface 318. Similar to the flexible substrate 214, the flexible substrate 314 includes embedded tracks on which both the ultrasound transducers 212 and the control logic dies 206 are mounted, thereby facilitating a thin profile and reduced overall thickness T4 (shown in FIG. 8) of the scanner assembly 300 in the flat configuration. The lateral arrangement of the ultrasound transducers 212 and the control logic dies 206 within a central portion 313 of the flexible substrate 214 is substantially similar to the scanner assembly 300. This lateral arrangement of the transducers 212 and the transducer control logic dies 206, where a transducer region 304 and a control region 308 are positioned side-by-side along a longitudinal width W7 of the flexible substrate, minimizes the overall stiff length L4 of the scanner assembly 300. In this embodiment, the stiff length L4 of the scanner assembly 300 comprises the length of the longest of the three stiff components included on the flexible substrate 214, which in this case is the length of the elongated wires 303. At least a portion of the scanner assembly 300, such as a slot 315 of the first transition region 310, the first transition region 310 itself, and/or the second transition region 302, can be shaped and sized to facilitate the rolling of the flexible substrate 314 into separate, nested cylinders, where each cylinder is formed from one of the support region 303, the control region 208, and the transducer region 304.

Figure 9:
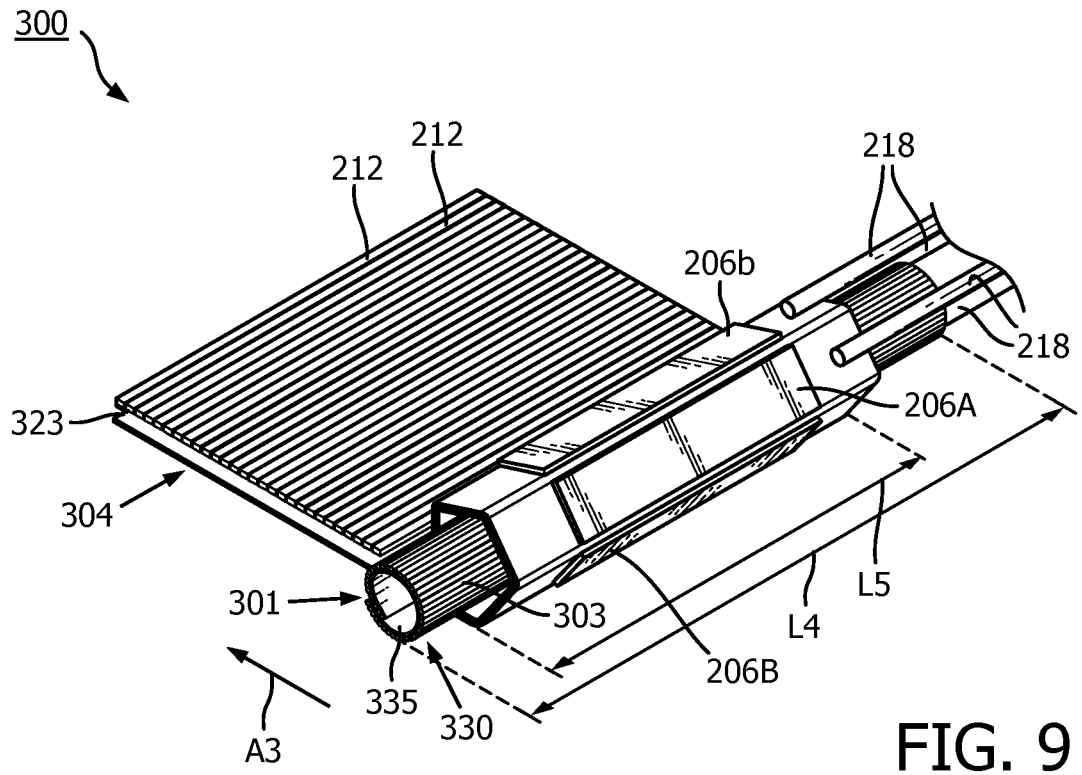
FIG. 9 is a diagrammatic perspective view of the scanner assembly shown in FIG. 8 in a partially rolled configuration, according to aspects of the present disclosure.
Figure 10:
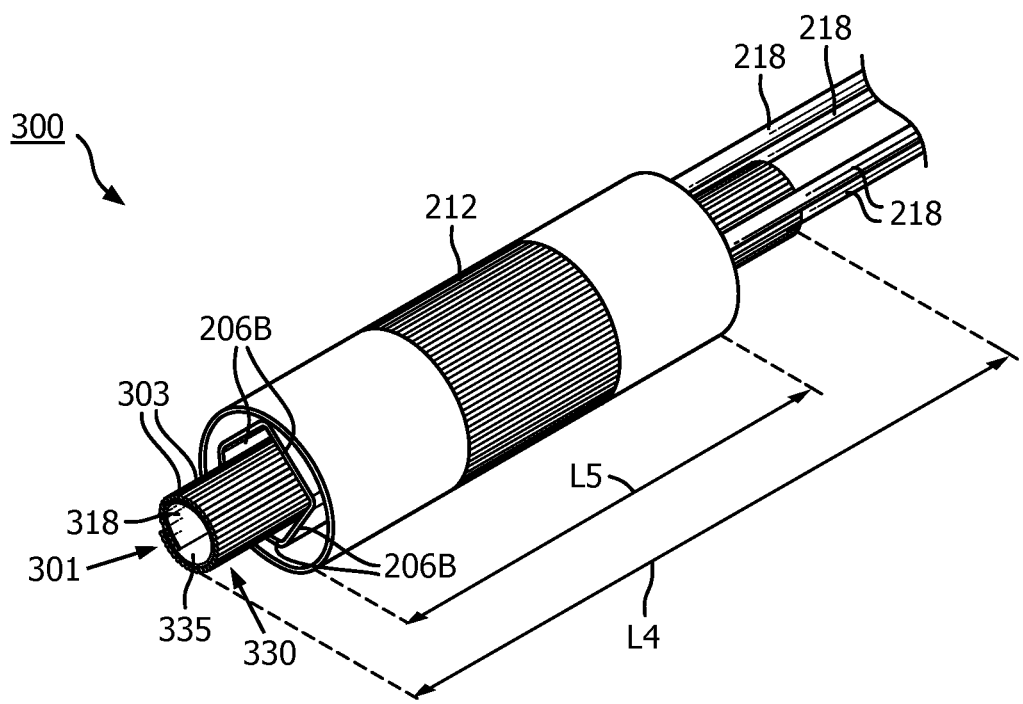
FIG. 10 is a diagrammatic perspective view of the scanner assembly shown in FIG. 8 in a rolled configuration, according to aspects of the present disclosure.
Figure 13:
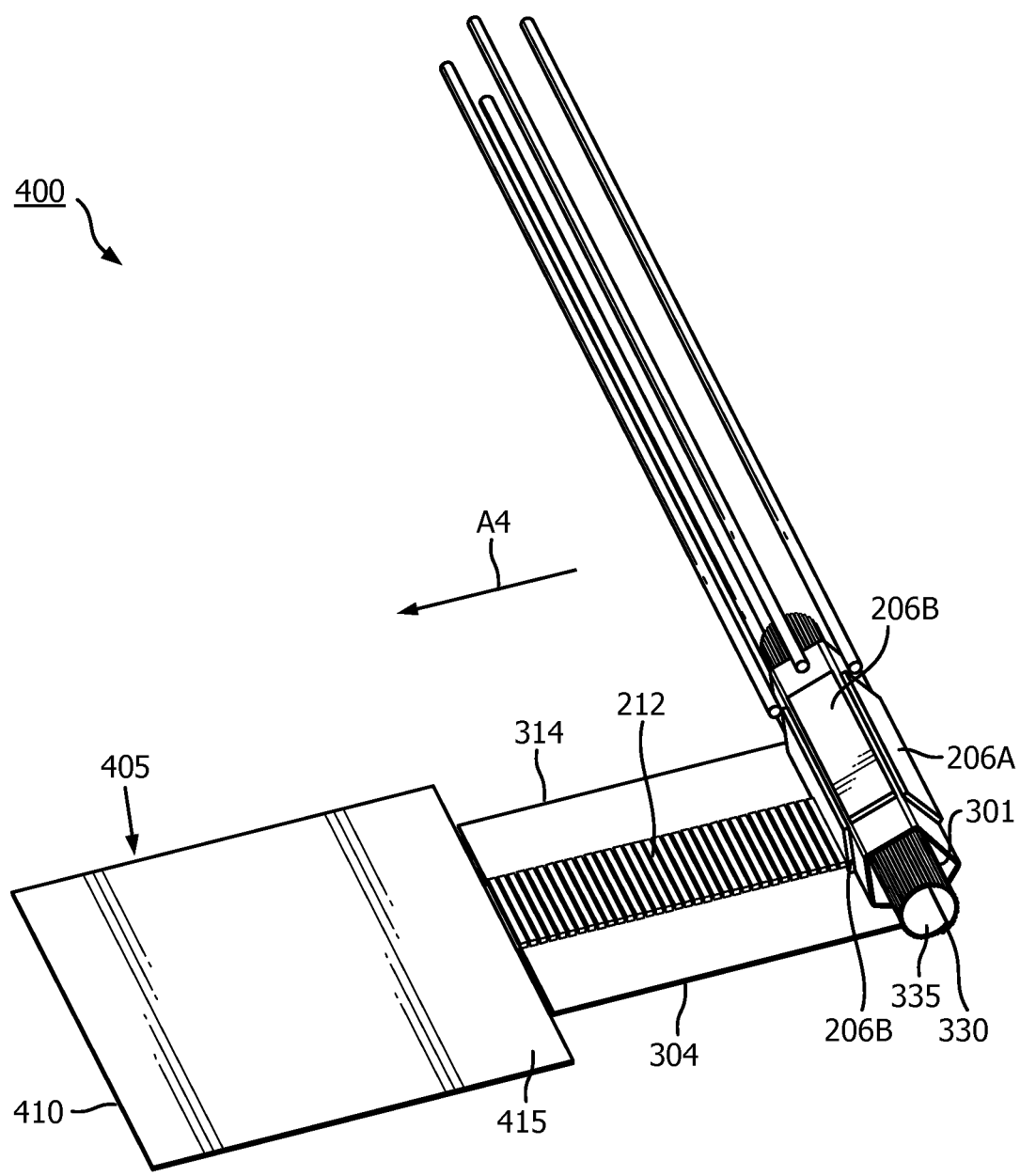
FIGS. 13, 14, and 15 illustrate the scanner assembly shown in FIG. 12 in a partially rolled configuration, according to aspects of the present disclosure. In particular.
Figure 14:
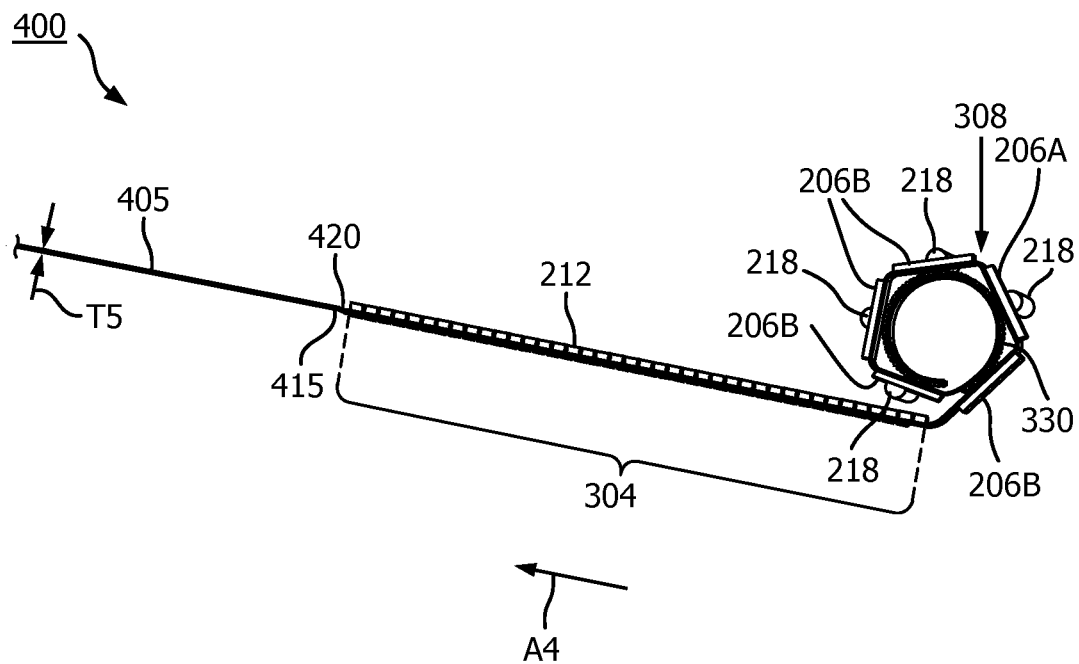
Figure 15:
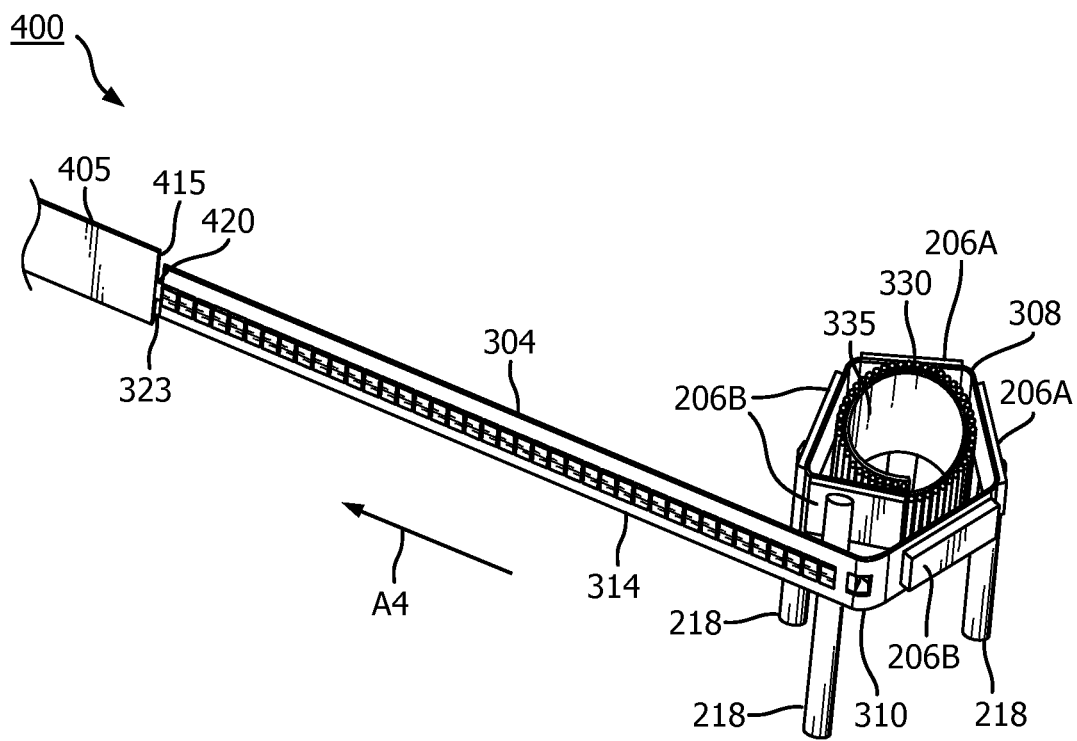

FIG. 9 is a perspective view of the scanner assembly 300 in a partially rolled configuration, according to aspects of the present disclosure. More views of the scanner assembly 300 in a partially rolled configuration are illustrated in FIGS. 13-15. FIG. 10 is a perspective view of a scanner assembly 300 in a completely rolled configuration, according to aspects of the present disclosure. Given the slender nature of the wires 303, the support region 310 is transformed or re-shaped into a very thin-walled support member 330 by rolling the inner edge 322 of the flexible substrate 314 in the direction of arrow A3. In the pictured embodiment, the support region 301 is rolled in the direction of the arrow A3 into a cylindrical support member 330 defining an integrated, wire-reinforced lumen 335. The luminal walls of the lumen 335 are formed by the second surface 318 of the support region 301 of flexible substrate 314. The inner edge 322 adjacent the support region 301 forms the inner edge of the roll. As shown in FIGS. 9 and 10, the length L4 of the support member 330 may exceed the length L5 of the main body 305 of the flexible substrate 314. In other embodiments, the length L5 of the support member 330 may be equal the length L4 of the main body 305 of the flexible substrate 314, thereby reducing the overall stiff length of the scanner assembly 300.

In the pictured embodiment, the second transition region 302 may be removed or the flexible substrate 314 may be sliced across the second transition region 302 to enable the support region 301 to be rolled into a perfectly cylindrical support member 330. In other embodiments, the second transition region 302 may form a bridge connecting the support member 330 to the remainder of the scanner assembly 300 (e.g., the control region 308 and the transducer region 304), and the support member 330 may be rolled into a spiral form. The second transition region 302 is a continuous portion of the flexible substrate 314, and provides a connection between the cylinder and the rolled prism.

The wires 303 are configured to lend sufficient stiffness to the flexible substrate 314 in the support region 310 to enable the wire-reinforced lumen of the support member 330 to adequately shield the guidewire during use of the IVUS device 102. The wires 303 provide mechanical reinforcement to the support member 330 as well as electrical shielding of the lumen 335. Moreover, the addition of the wire-reinforced support region 301 to the flexible substrate 314 eliminates the need for a separate support member (e.g., the support member 230 shown in FIGS. 3-6). Thus, embodiments with an integrated, wire-reinforced support region 301 provide for a scanner assembly 300 having a reduced profile and overall diameter by reducing the overall diameter of the support member. Embodiments with an integrated, wire-reinforced support region 301 also allow for a more flexible distal tip of the IVUS imaging device 102 by providing a more flexible support member than the conventional rigid support member (e.g., the support member 230 described above with reference to FIGS. 2-6). In addition, embodiments with an integrated, wire-reinforced support region 301 enhance manufacturing of the scanner assembly 300 by facilitating ease of assembly (e.g., by decreasing the complexity and number of parts of the scanner assembly and reducing the time required for manufacture) and by decreasing costs of manufacture.

Figure 11:
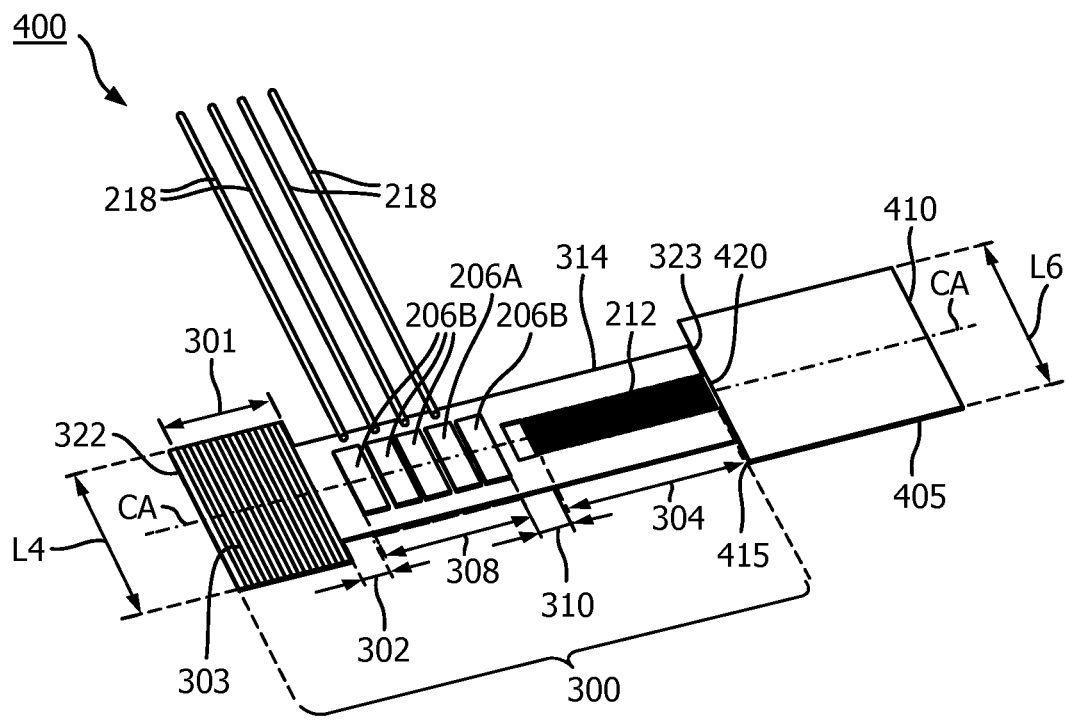
FIG. 11 is a diagrammatic perspective view of the top of another exemplary scanner assembly in a flat configuration, according to aspects of the present disclosure.
Figure 12:
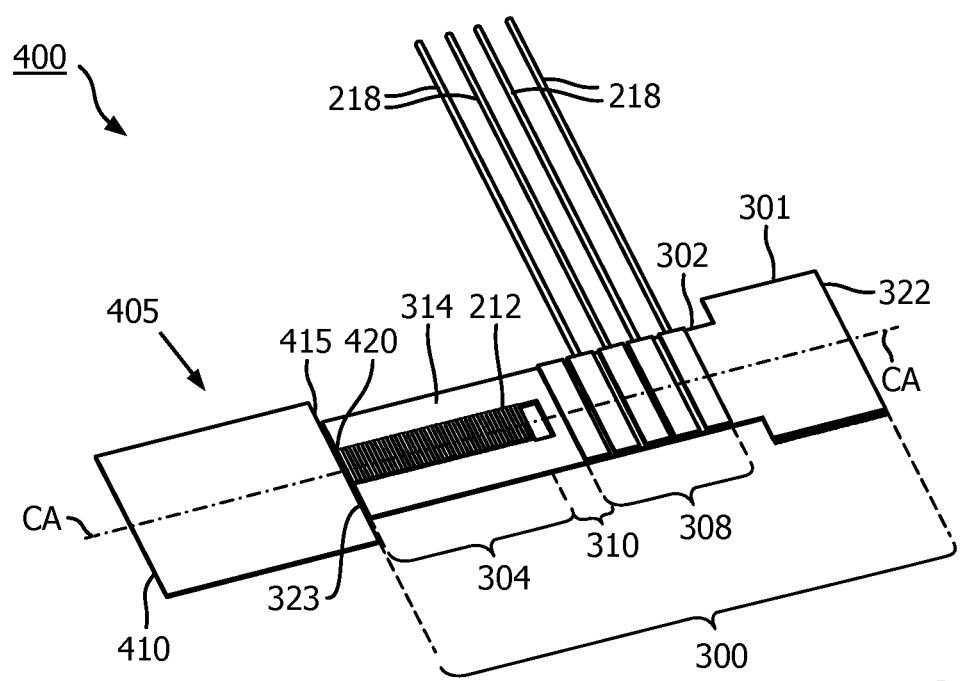
FIG. 12 is a diagrammatic perspective view of the bottom of the scanner assembly shown in FIG. 11 in a flat configuration, according to aspects of the present disclosure.

FIG. 11 is a diagrammatic perspective view of the top of an exemplary scanner assembly 400 in a flat configuration, according to aspects of the present disclosure. FIG. 12 is a diagrammatic perspective view of the bottom of the scanner assembly 400 in a flat configuration, according to aspects of the present disclosure. Several IVUS imaging devices, such as those including cMUT arrays, utilize an outer window or outer shield to contain adequate acoustic matching medium and to provide adequate electrical and mechanical protection to the imaging components.

The scanner assembly 400 comprises an outer window region 405 attached to an exemplary flexible substrate embedded with imaging components in any of a variety of configurations suitable for intravascular imaging. In the pictured embodiment, for the sake of simplicity, the scanner assembly 400 comprises the outer window region 405 coupled to the scanner assembly 300 described above with respect to FIGS. 7-10. In the pictured embodiment, the outer window region 405 is formed as an integrated part of the flexible substrate 314. The outer window region 405 is disposed adjacent the transducer region 304 at the outer edge 323 of the flexible substrate 314. The outer window region 405 extends from an outer window edge 410 to an inner window edge 415. The inner window edge 415 of outer window region 405 is coupled to the outer edge 323 of the flexible substrate 314. In the pictured embodiment, a third transition region 420 forms a bridge between the outer window region 405 and the transducer region 304 of the flexible substrate 314. The third transition region 420 is shaped as a rectangular portion of flexible substrate and/or window material. In other embodiments, the scanner assembly 400 lacks a third transition region 420, and the outer window region 405 is coupled directly to the transition region 304.

In the flat configuration illustrated in FIGS. 11 and 12, the outer window region 405 has a generally rectangular shape. Although the outer window region 405 is shown herein as having a generally rectangular shape, other embodiments may include an outer window region having alternative shapes (e.g., square). The outer window region 405 has a length L6. The length L6 measures between 2 and 5 mm. The length L6 may be equal or greater in length than the length L4 of the wire-reinforced support region 301 of the scanner assembly 300. In the pictured embodiment, the length L6 is equal to the length L4. In some embodiments, the outer window region 405 is formed atop an extension of the flexible substrate 314. Materials for the outer window region 405 may be selected for their biocompatibility, durability, hydrophilic or hydrophobic properties, low-friction properties, ultrasonic permeability, and/or other relevant criteria. For example, the outer window region 405 may include Parylene™. Other suitable materials include polyester, polyethylene, or Polyimide.

FIGS. 13, 14, and 15 illustrate the scanner assembly shown in FIG. 12 in a partially rolled configuration, according to aspects of the present disclosure. In particular, FIG. 13 is a diagrammatic perspective view of the scanner assembly, FIG. 14 is a side view of the scanner assembly, and FIG. 15 is an oblique view of the scanner assembly. In the pictured embodiment, the scanner assembly 300 is rolled in the direction of the arrow A4, rolling the support region 301 into a cylindrical support member 330 defining an integrated, wire-reinforced lumen 335, and rolling the control region 308 into a pentagonal prism shape. As indicated in FIG. 14, the outer window region 405 includes a thickness T5 which may be smaller or larger than the thickness T3 of the remainder of the flexible substrate T3 (shown in FIG. 8). In some embodiments, the thickness T3 measures between 2 and 10 microns.

Figure 16:
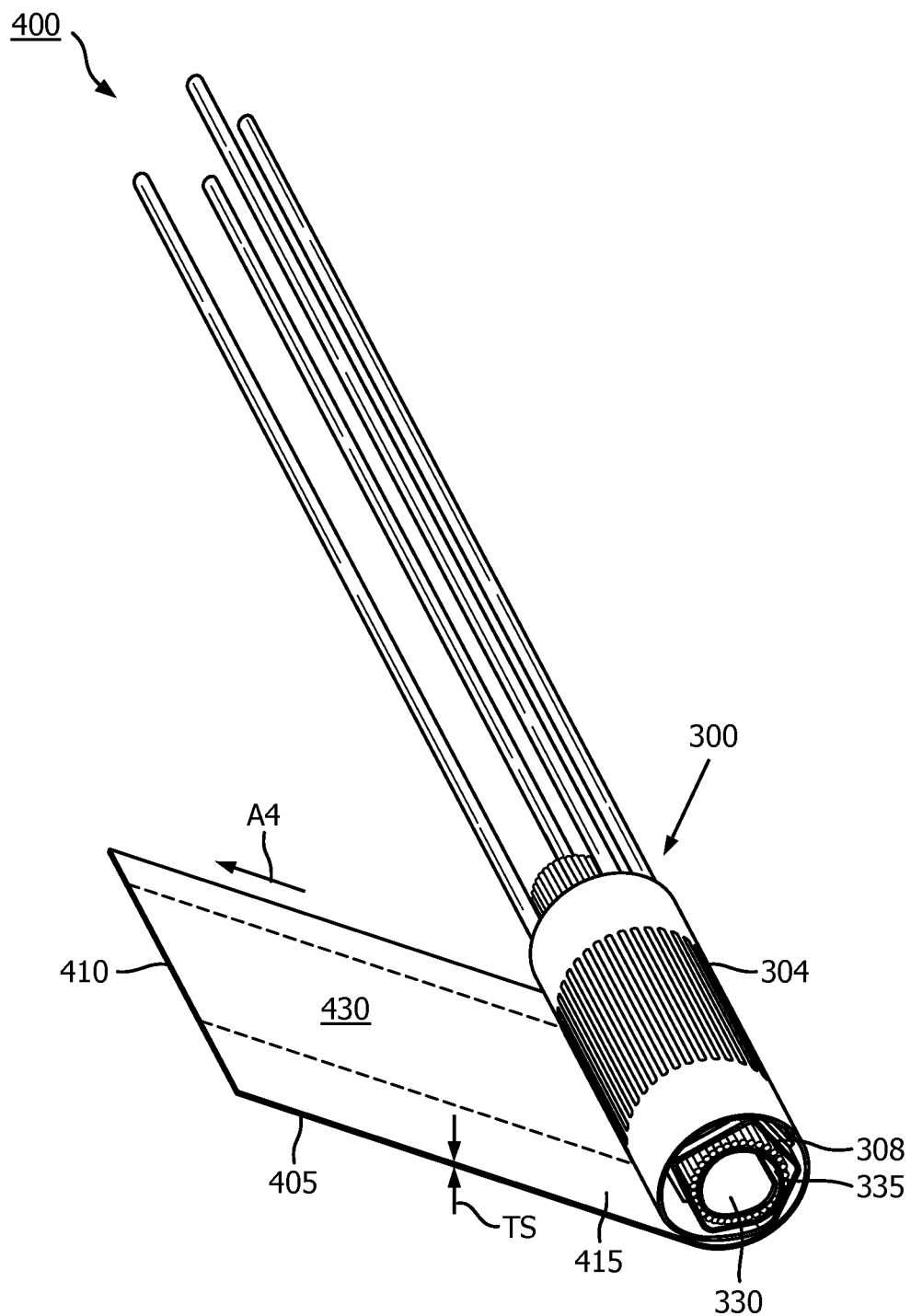
FIGS. 16, 17, and 18 illustrate the scanner assembly shown in FIG. 12 in a rolled configuration, according to aspects of the present disclosure. In particular.
Figure 17:
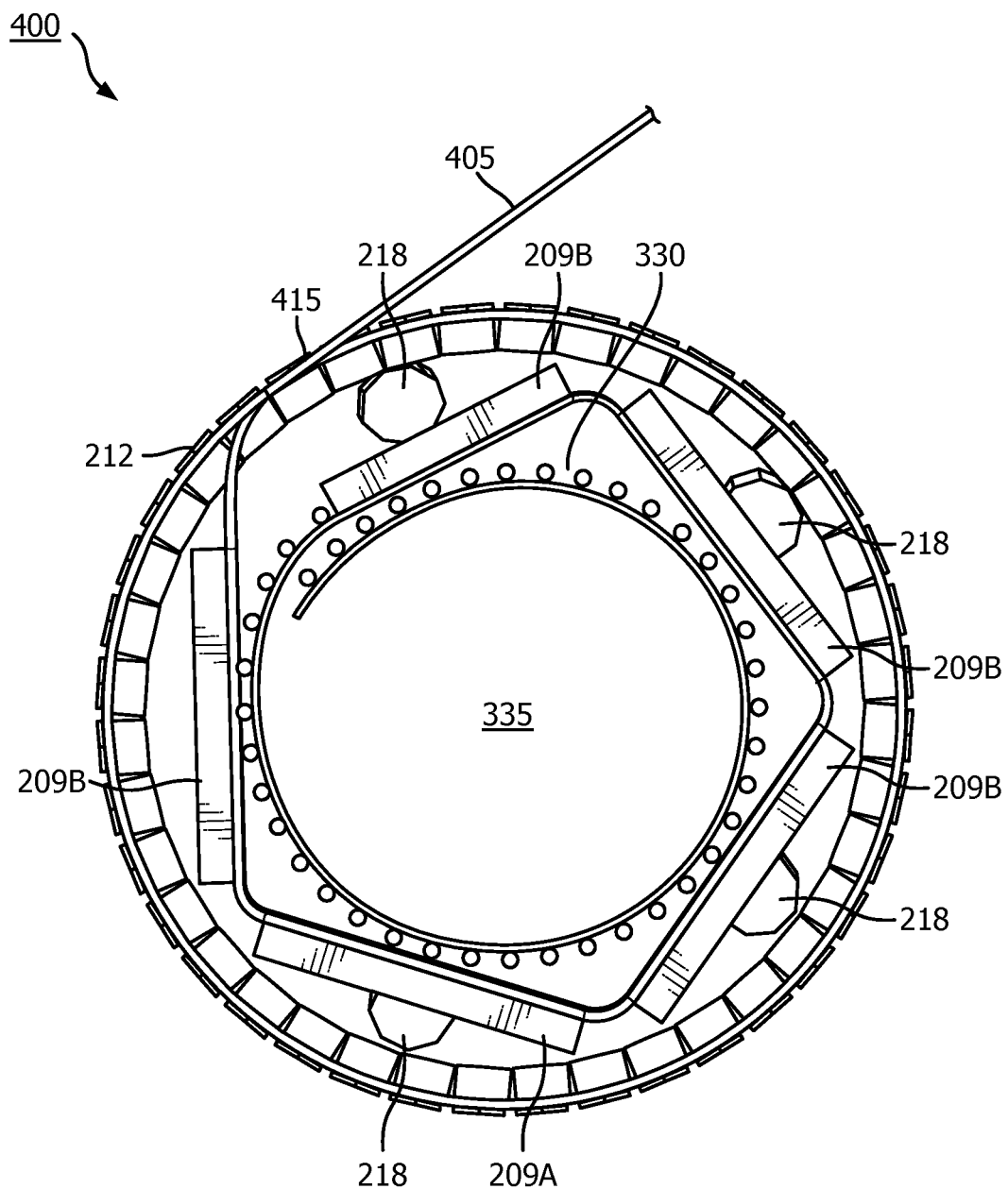
Figure 18:
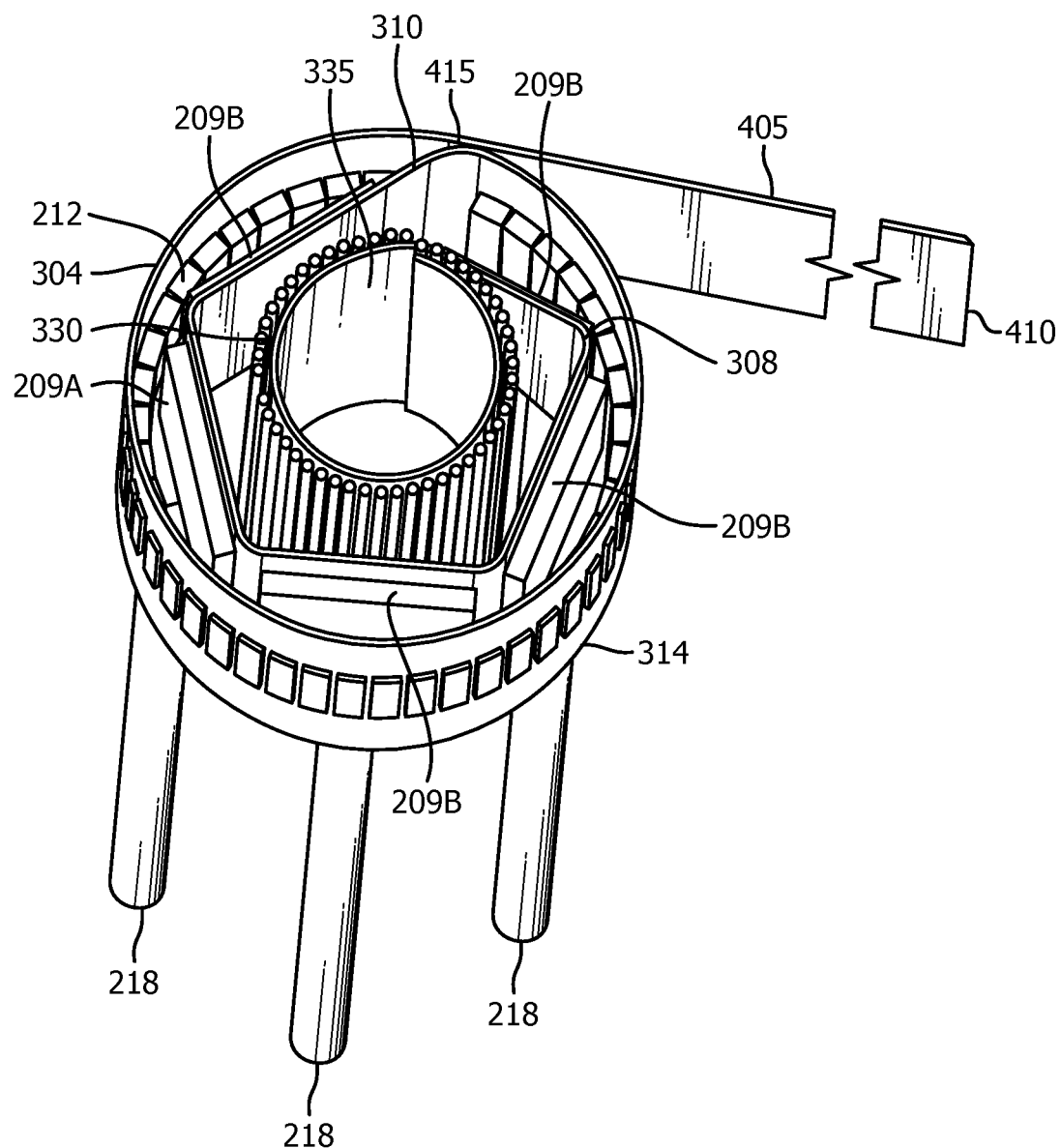

FIGS. 16, 17, and 18 illustrate the scanner assembly shown in FIG. 12 in a rolled configuration, according to aspects of the present disclosure. In particular, FIG. 16 is a diagrammatic perspective view of the scanner assembly, FIG. 17 is a side view of the scanner assembly, and FIG. 18 is an oblique view of the scanner assembly. The outer window region 405 provides a protective layer around the electrical and mechanical components of the scanner assembly 300 when the scanner assembly 400 assumes a rolled configuration as shown in FIGS. 16-18. In a rolled configuration, the scanner assembly 400 has an outer profile that is substantially cylindrically-shaped. The outer surfaces of the outer window region 405, the transducer region 304, and the control region 308 may form a continuous, spiral surface. Other configurations of the outer window region 405 is also contemplated. For example, in other embodiments, the flexible substrate 314 may be sectioned and separated from the outer window region 405, which may form a separate, annular cylinder around the scanner assembly 300. In some embodiments, the window region 405 may vary in thickness along its length L6. For example, in some embodiments, the thickness T5 of the outer window region 405 may be greater in a transducer window region 430 positioned to overlay the transducer region 304 (i.e., the outer window region 405 may be thicker in areas overlaying the transducer region 304 than the areas overlaying the proximal portion 209 or distal region 211 of the flexible substrate 314). Thus, the outer window region 405 acts as a shield that circumferentially encases the scanner assembly 300 and protects it from the surrounding environment during use. Embodiments with an integrated, outer window region 405 enhance manufacturing of the scanner assembly 400 by facilitating ease of assembly (e.g, by decreasing the complexity and number of parts of the scanner assembly and reducing the time required for manufacture) and by decreasing costs of manufacture.

Figure 19:
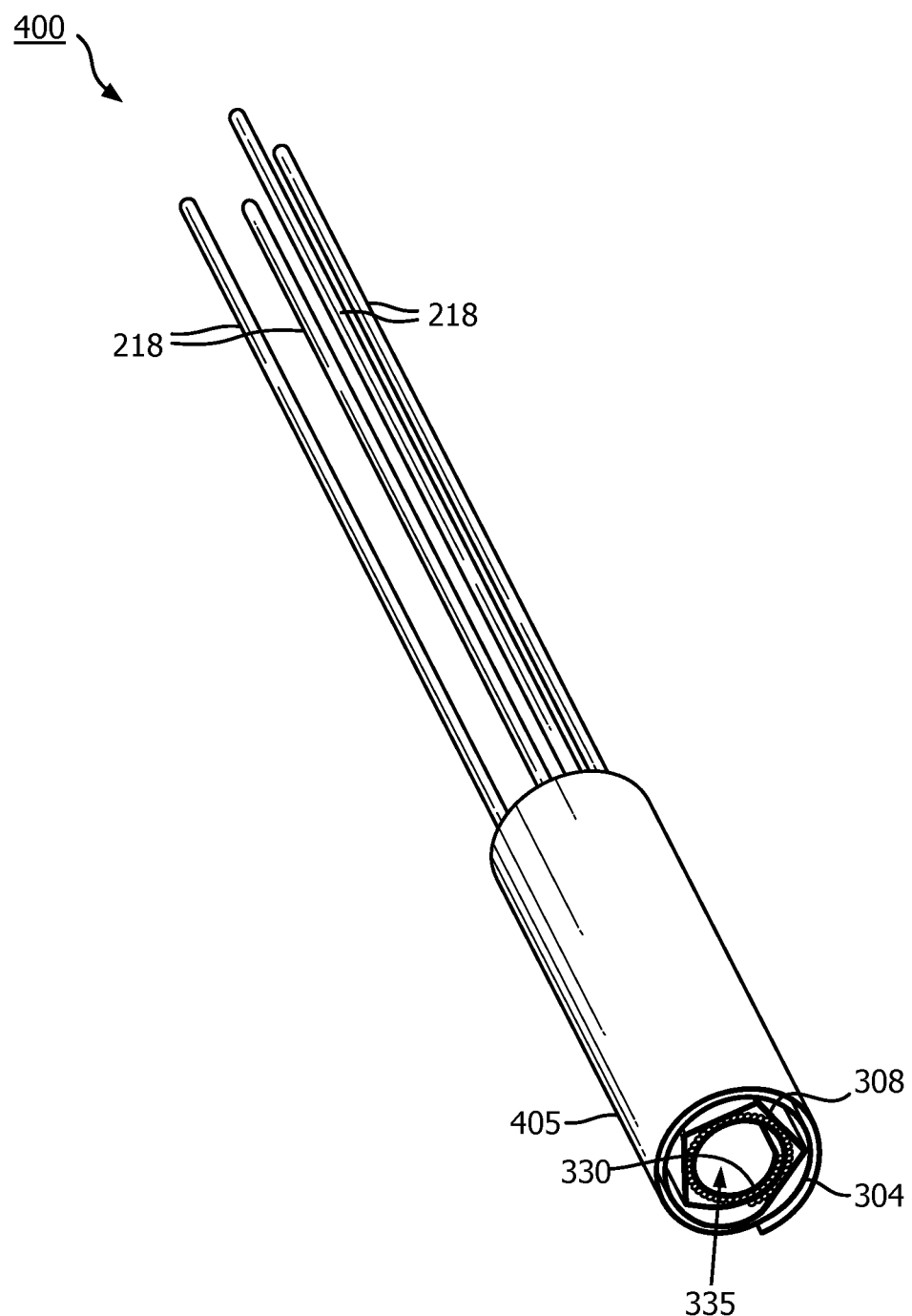
FIGS. 19 and 20 illustrate the scanner assembly shown in FIG. 12 in a rolled configuration, according to aspects of the present disclosure. In particular.
Figure 20:
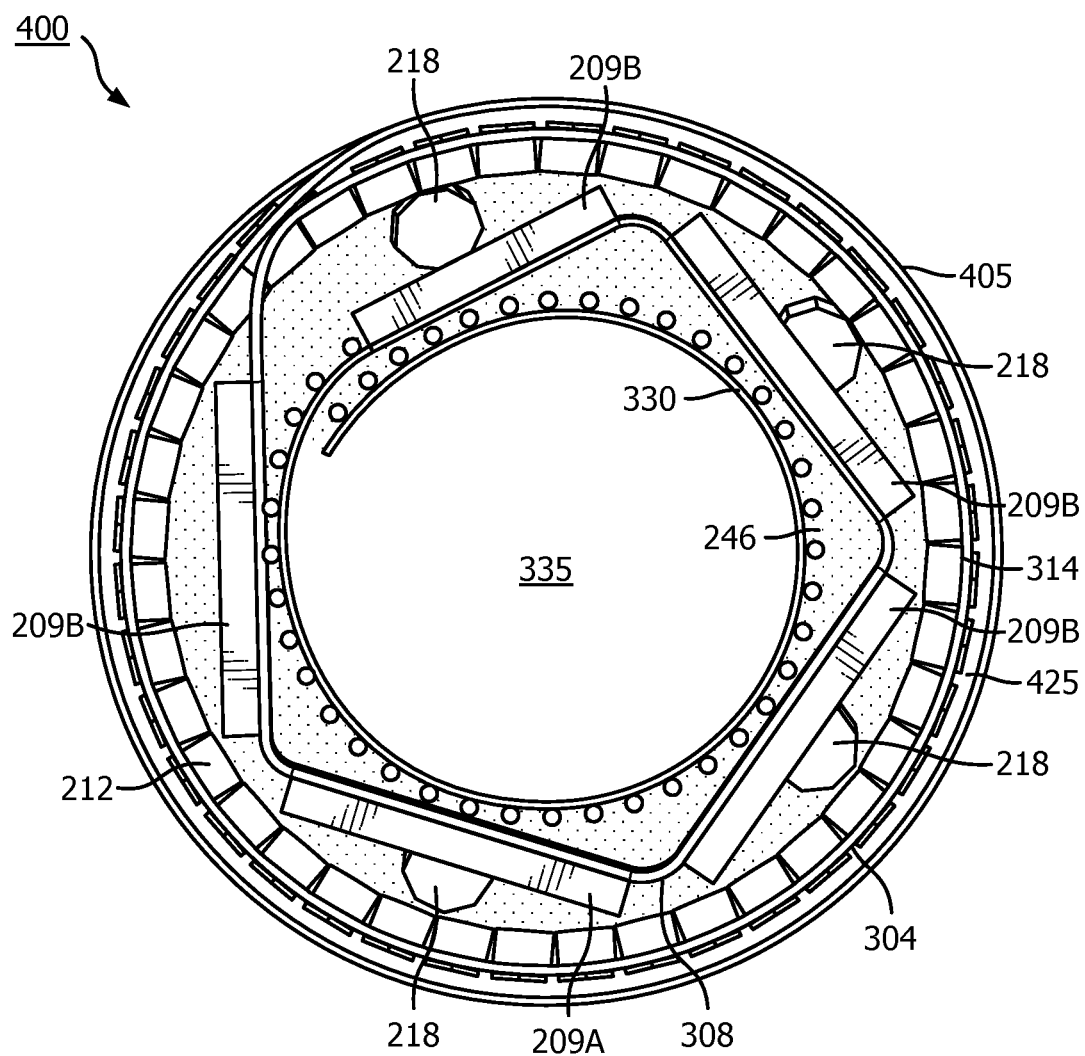

FIGS. 19 and 20 illustrate the scanner assembly 400 in a rolled configuration, according to aspects of the present disclosure. In particular, FIG. 19 is a diagrammatic perspective view of the scanner assembly 400, and FIG. 20 is a diagrammatic front view of a distal portion of the scanner assembly 400. The outer window 405 acts to contain acoustic matching medium 425 between the outer window region 405 and the transducer region 304. In other embodiments, the scanner assembly 400 may include a scanner assembly other than the scanner assembly 300. For example, the scanner assembly 400 need not include a wire-reinforced support member 330. Regardless, embodiments with an integrated, outer window region 405 provide for a scanner assembly 400 having a reduced profile by reducing the overall diameter of the support member. Embodiments with an integrated, outer window region 405 may allow for a more flexible distal tip of the IVUS imaging device 102 by providing a more flexible window region than conventional outer membranes. In addition, embodiments with an integrated, outer window region 405 enhance manufacturing of the scanner assembly 400 by facilitating ease of assembly (e.g., by decreasing the complexity and number of parts of the scanner assembly and reducing the time required for manufacture) and by decreasing costs of manufacture.

Conventional scanner assemblies may include phased array transducer elements (i.e., an array of transducer elements wrapped or positioned around a central lumen) positioned on a substrate to include trenches defined by the perpendicular side walls of individual transducer elements. By using a flexible substrate with embedded metal tracks on which the ultrasound transducer elements are manufactured, it is possible to roll such a flexible transducer array into a desirable form factor with a very small diameter. Such transducer arrays may consist of rigid silicon islands or silicon strips on which the transducers are built, and flexible substrates connecting adjacent strips at their top side. Trenches are created between the transducer elements, and the trenches are defined by the opposing sidewalls of the adjacent strips. Typically, the trenches between adjacent elements are realized by means of deep reactive ion etching ("DRIE"), which generally renders straight sidewalls that are perpendicular to the substrate surface (i.e., the silicon surface). When these flexible transducer arrays are shaped into a convex shape (e.g., a cylinder), the bottom edges of opposing sidewalls of adjacent transducer elements (i.e., adjacent transducer strips or islands) may collide, thus limiting the attainable radius of curvature. The perpendicular trenches can cause unwanted buckling upon curvature of the transducer elements as the transducer elements contact one another upon curving the substrate. Moreover, perpendicular sidewalls between neighboring transducer elements cause the transducer elements to only partially abut one another upon curving or flexing the substrate, thereby minimizing the potential curvature of the substrate and minimizing the surface area available for transducer elements. This collision and resultant radius of curvature depends upon several factors, including trench width, transducer element thickness, and the desired radius of curvature. For optimal mechanical robustness, the individual transducer elements (i.e., transducer islands or strips) need to have a certain minimum thickness (for example, without limitation, 40 μm). The thickness may range between 30 and 50 microns. To achieve a smaller radius of curvature for a given thickness of the transducer elements, the trench width would need to be increased. However, increasing the trench width or separation between the transducer elements would undesirably reduce the usable active transducer region on the substrate. Alternatively, including non-perpendicular and/or non-straight sidewalls, such that the bottom edges of the transducer elements are spaced further apart than the top edges of the transducer elements (i.e., where the transducer elements connect to the substrate), enables the use of narrow trenches on tightly curved transducers without the risk of colliding opposing bottom edges. This arrangement preserves the maximum surface area of the substrate for active transducer use while also providing for a smaller overall diameter of the rolled transducer region. This advantage increases with a decreasing transducer diameter.

Figure 21:
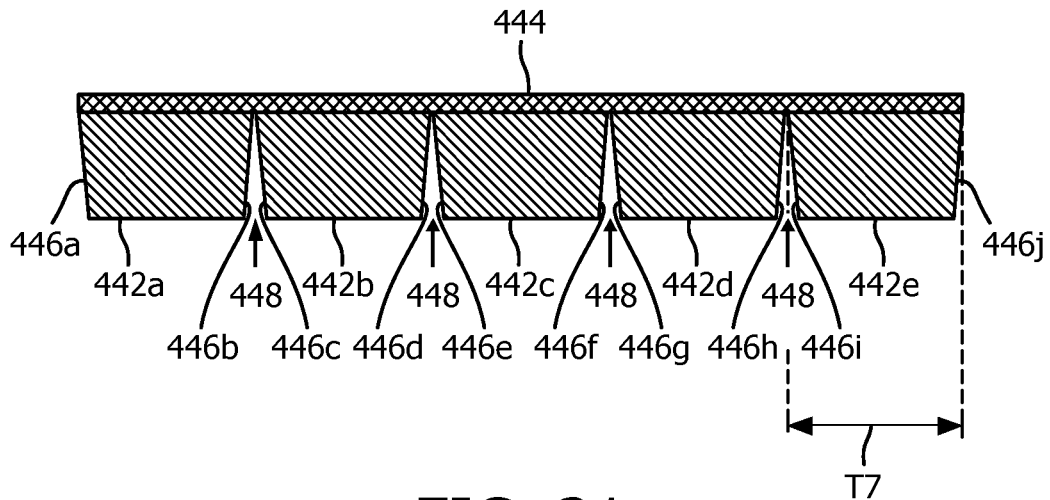
FIGS. 21 and 22 illustrate exemplary transducers arranged on an exemplary flexible substrate according to aspects of the present disclosure. In particular.
Figure 22:
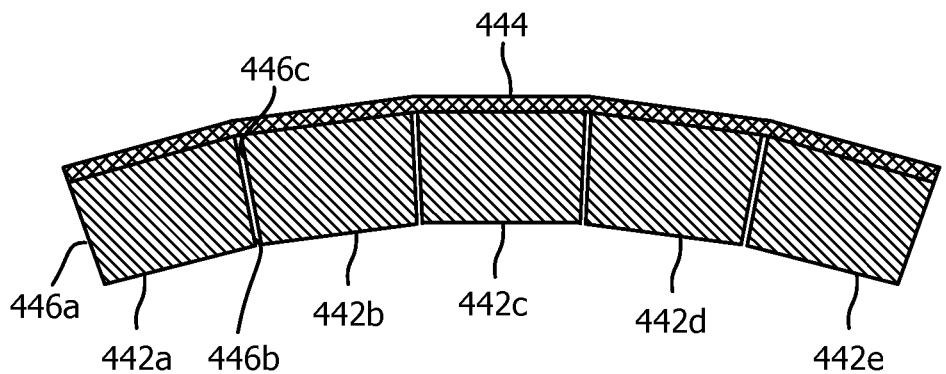

FIGS. 21 and 22 illustrate an array 440 of transducer elements 442 arranged on a substrate 444 according to aspects of the present disclosure. In particular, FIG. 21 is a diagrammatic side view of the array 440 of transducer elements 442a-e with the substrate 444 in a flat configuration, and FIG. 22 is a diagrammatic side view of the array 440 of transducer elements 442a-e with the substrate 444 in a curved (or rolled) configuration. As shown in FIG. 21, the transducer elements 442a-e are arranged linearly on the substrate 444. In some embodiments, the substrate 444 comprises a flexible substrate. The transducer elements 442 include a thickness T7. The thickness T7 may range from 30 to 50 microns. The transducer elements 442a-e include angled sidewalls 446a-j. The sidewalls 446 are non-perpendicular to one another, thereby defining wedge-shaped trenches 448 between the non-perpendicular sidewalls 446. In some examples, the sidewalls 446 can be angled approximately between 1° and 45°, between 1° and 30°, between 1° and 15°, between 1° and 10°, between 1° and 5°, including values such as 22.5°, 11.25°, 9°, 5.625°, 4.5°, 2.8125°, and/or other suitable values, both larger and smaller. The angle of the sidewalls 446 can be based on the number of transducer elements 442, the diameter of the scanner assembly 110, the diameter of the imaging device 102, the dimensions of the transducer elements 442, the spacing between adjacent transducer elements 442, etc. In some embodiments, the sidewalls 446 of all transducer elements can be angled by the same amount. In other embodiments, the sidewalls 446 of different transducers elements are angled by different amounts.

As shown in FIG. 22, when the substrate 444 is curved or flexed, the transducer elements 442 contact one another along the entire length of their sidewalls. For example, the sidewall 446b of the transducer element 442a comes into full contact with the sidewall 446c of the transducer element 442b. Thus, this non-perpendicular trench configuration maximizes the surface area available on the substrate for the transducer elements 442. Other non-perpendicular separations of the transducer elements 442 are contemplated. For example, in some embodiments, the sidewalls 446 may be curved or serpentine, where neighboring sidewalls 446 are configured to rest against one another or contact one another along at least a portion of the length of the trench 448 when the flexible substrate 444 is flexed or in a curved configuration. One method of manufacture may be anisotropic dry etching or an appropriate combination of anisotropic dry etching and isotropic dry etching, such that the desired trench sidewall profile is obtained.

Figure 23:
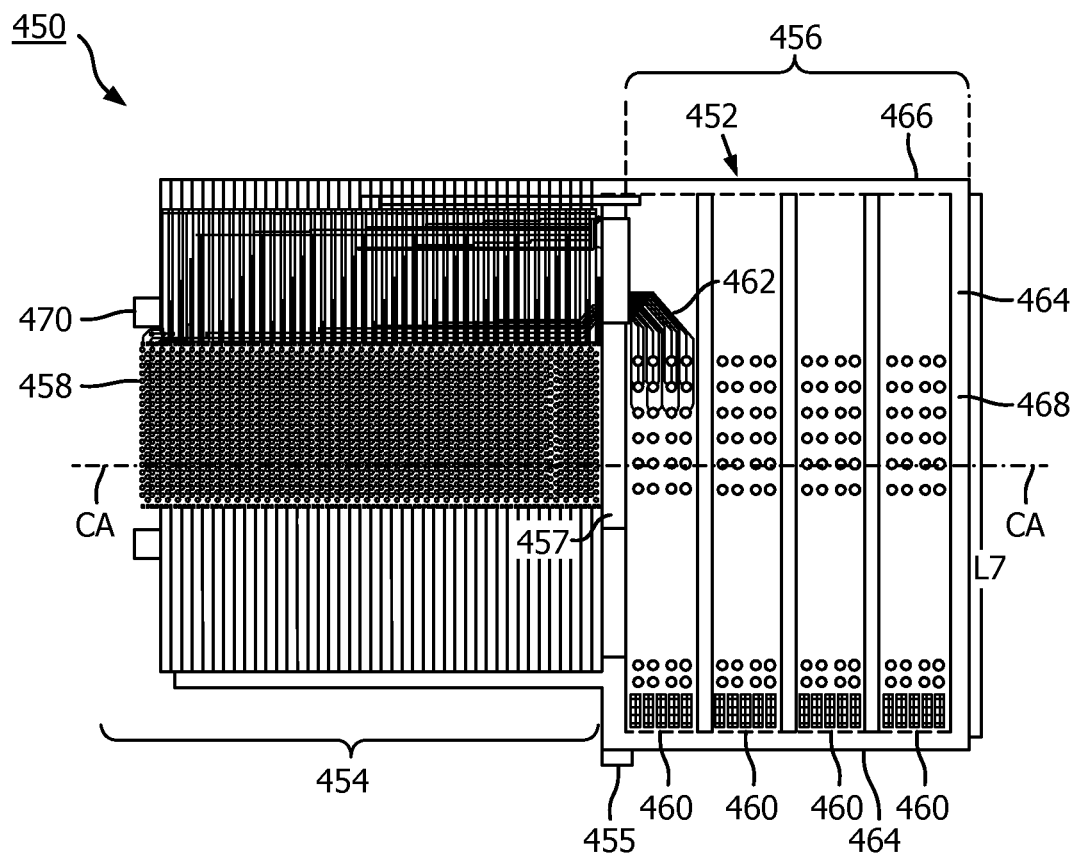
FIG. 23 is a diagrammatic top view of an exemplary scanner assembly in a flat configuration, according to aspects of the present disclosure.

FIG. 23 is a diagrammatic top view of an exemplary scanner assembly 450 in a flat configuration, according to aspects of the present disclosure. The scanner assembly 450 is substantially similar to the scanner assembly 110 described above with reference to FIGS. 2-6. The assembly 450 includes a flexible substrate 452 embedded with tracks defining a control region 456, a transducer region 454, and a transition region 455. The flexible substrate 452 is shown in an unrolled or flat configuration. The transducer region 454 includes a transducer array 458. The control region 456 includes transducer control logic dies 460. The transition region 455 is disposed between the transducer region 454 and the control region 456. The transition region 410 includes a slot or cutout 457. The flexible substrate 452 includes multiple conductive traces 462 configured to connect the transducer array 458 and the transducer control logic dies 460. The transducer array 458 is a non-limiting example of a medical sensor element and/or a medical sensor element array. The transducer control logic dies 460 is a non-limiting example of a control circuit.

In the embodiment shown in FIG. 23, the transducer region 454, the transition region 455, and the control region 456 are laterally disposed (or stacked) adjacent one another within a central portion 464 of the flexible substrate 452. The central portion 464 of the flexible substrate 452 extends between a proximal edge 464 and a distal edge 466 of the flexible substrate. Both the transducer region 454 and the control region 456 are aligned along a central axis CA extending through the central portion 464 from an inner edge 468 to an outer edge 470 of the flexible substrate 452. The transducer region 454 is disposed adjacent the outer edge 470 of the flexible substrate 452. The control region 456 is disposed adjacent the inner edge 468 of the flexible substrate 452. In some embodiments, the transducer region 454 and/or the control region 456 may be spaced apart from the outer edge 470 and the inner edge 468, respectively, of the flexible substrate 452. Thus, the transducer array 458 is positioned laterally (or stacked) relative to the transducer control logic dies 460 within the central portion 464 of the flexible substrate 452. This lateral arrangement of the transducer array 458 and the transducer control logic dies 460, where the transducer region 454 and the control region 456 are positioned side-by-side along a longitudinal width of the flexible substrate, minimizes the overall longitudinal length and the overall stiff length of the scanner assembly 450. In this embodiment, the stiff length L8 of the scanner assembly 450 comprises the length of the longer of the two stiff components included on the flexible substrate 452, which in this case is the length of the transducer control logic dies 460.

Figure 24A:
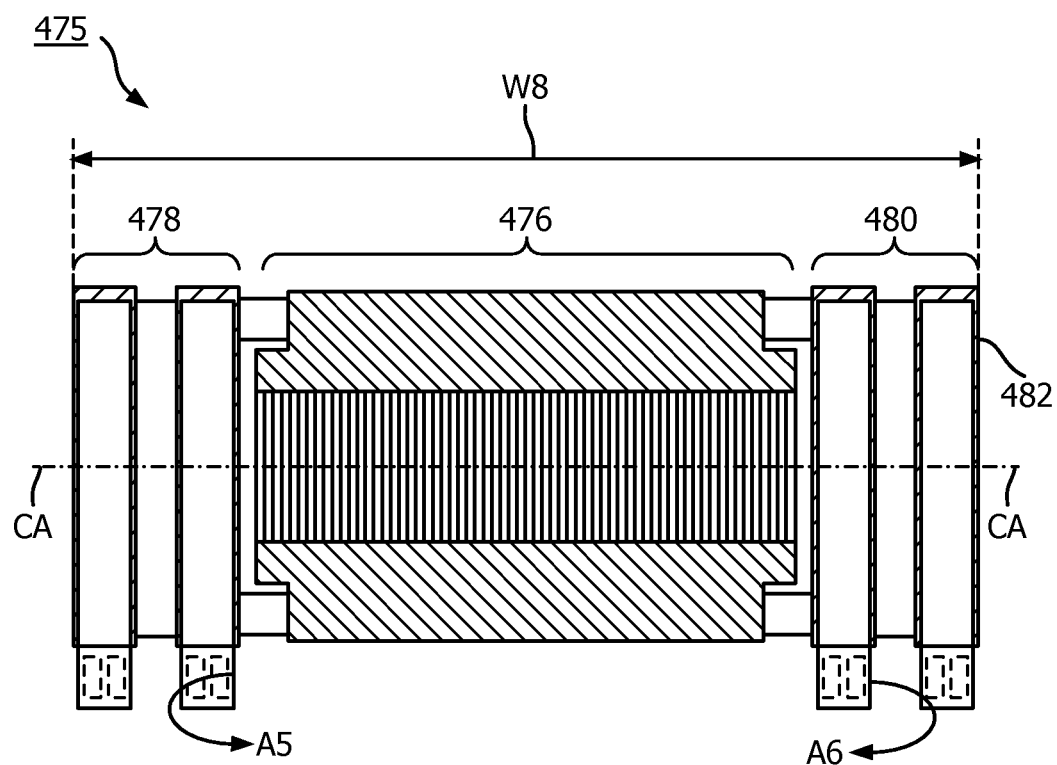
FIGS. 24a and 24b illustrate another exemplary scanner assembly, according to aspects of the present disclosure. In particular.
Figure 24B:
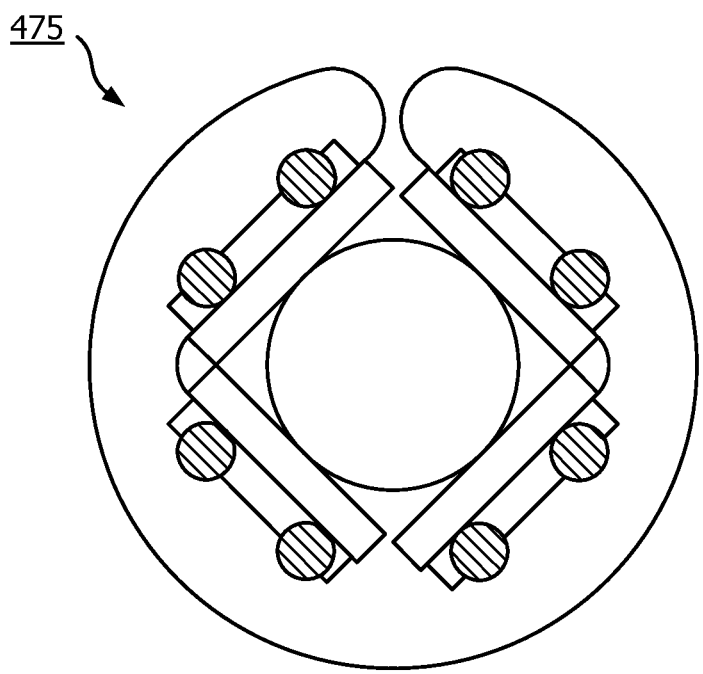

FIGS. 24a and 24b illustrate an exemplary scanner assembly 475, according to aspects of the present disclosure. In particular, FIG. 24a is a diagrammatic top view of the scanner assembly 475 in a flat configuration, and FIG. 24b is a diagrammatic front view of a distal portion of the scanner assembly 475 in a rolled configuration. As shown in FIG. 24a, the scanner assembly 475 is assembled in a "double stacking" configuration, where a transducer region 476 is bracketed on both sides by two separate control regions 478, 480. In the pictured embodiment, a flexible substrate 482 includes the first control region 478, the transducer region 480, and the second control region 480 arranged laterally (e.g., side-by-side) along a central axis CA extending through the flexible substrate 482 from a first edge 484 to a second edge 486. The central axis CA extends in parallel with a longitudinal width W8 of the flexible substrate 482. As shown in FIG. 24b, the scanner assembly 475 assumes a rolled configuration when each control region 478 and 480 is rolled in an opposite direction in the directions of arrows A5 and A6 to form an annular cylindrical shape. This embodiment gives shorter leads between CMUT elements and the control electronics.

Figure 25:
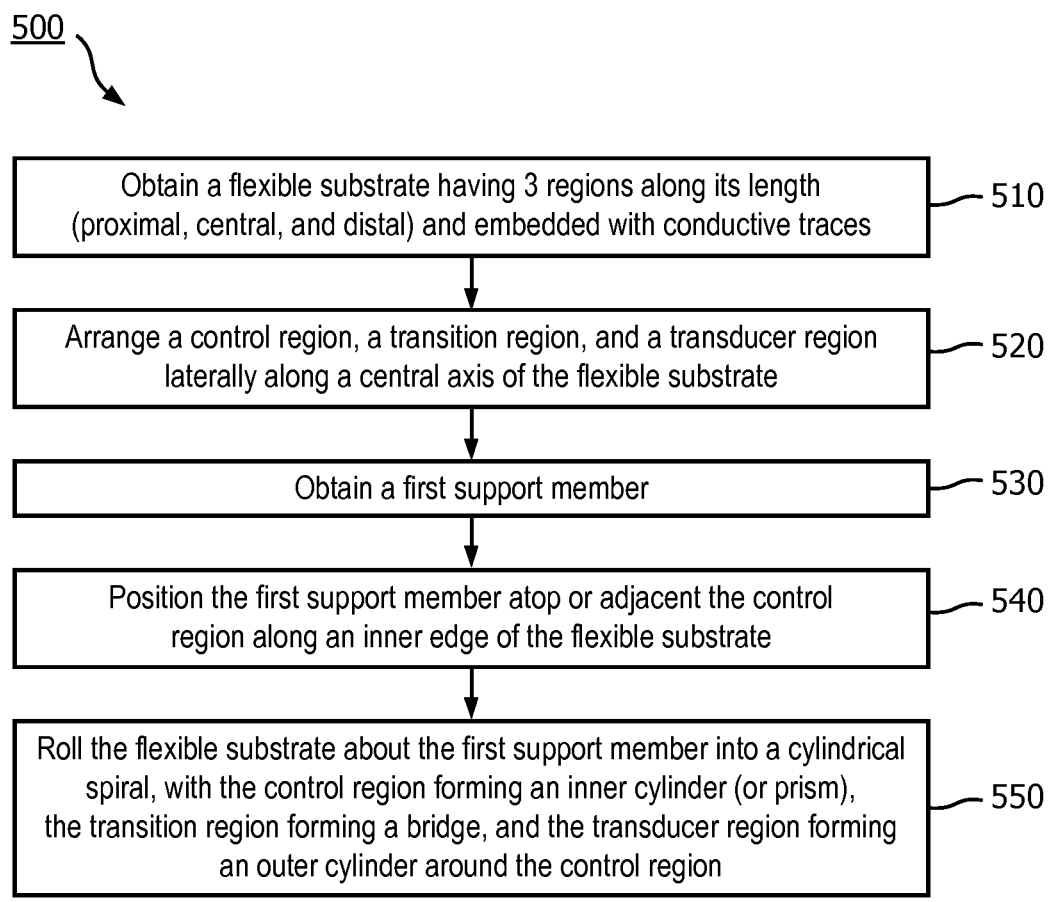
FIG. 25 is a flow diagram of a method of assembling an ultrasound imaging device according to an embodiment of the present disclosure.

FIG. 25 is a flow diagram of a method 500 of assembling an intravascular imaging device. It is understood that the steps of method 500 may be performed in a different order than shown in FIG. 25, additional steps can be provided before, during, and after the steps, and/or some of the steps described can be replaced or eliminated in other embodiments. The steps of the method 500 can be carried out by a manufacturer of the intravascular imaging device.

At step 510, the method 500 includes obtaining a flexible substrate embedded with conductive traces for coupling a transducer region to a control region. The flexible substrate may be configured to include three distinct regions extending along its length: a proximal portion, a central portion, and a distal portion.

At step 520, a control region, a transition region, and a transducer region are arranged laterally along a central axis of the flexible substrate. In some embodiments, the transducer region, the transition region, and the control region are arranged side-by-side within the central portion of the flexible substrate.

At step 530, a first support member is obtained. In some embodiments, the first support member is separate from the flexible substrate. It may be sized and shaped so that the flexible substrate can be wrapped around it to form a generally cylindrical scanner assembly.

At step 540, the first support member is laid atop or adjacent the control region along an inner edge of the flexible substrate.

At step 550, the flexible substrate is rolled or wrapped about the first support member into a cylindrical spiral, with the control region forming an inner cylinder (or prism), the transition region forming a bridge, and the transducer region forming an outer cylinder around the control region.

Figure 26:
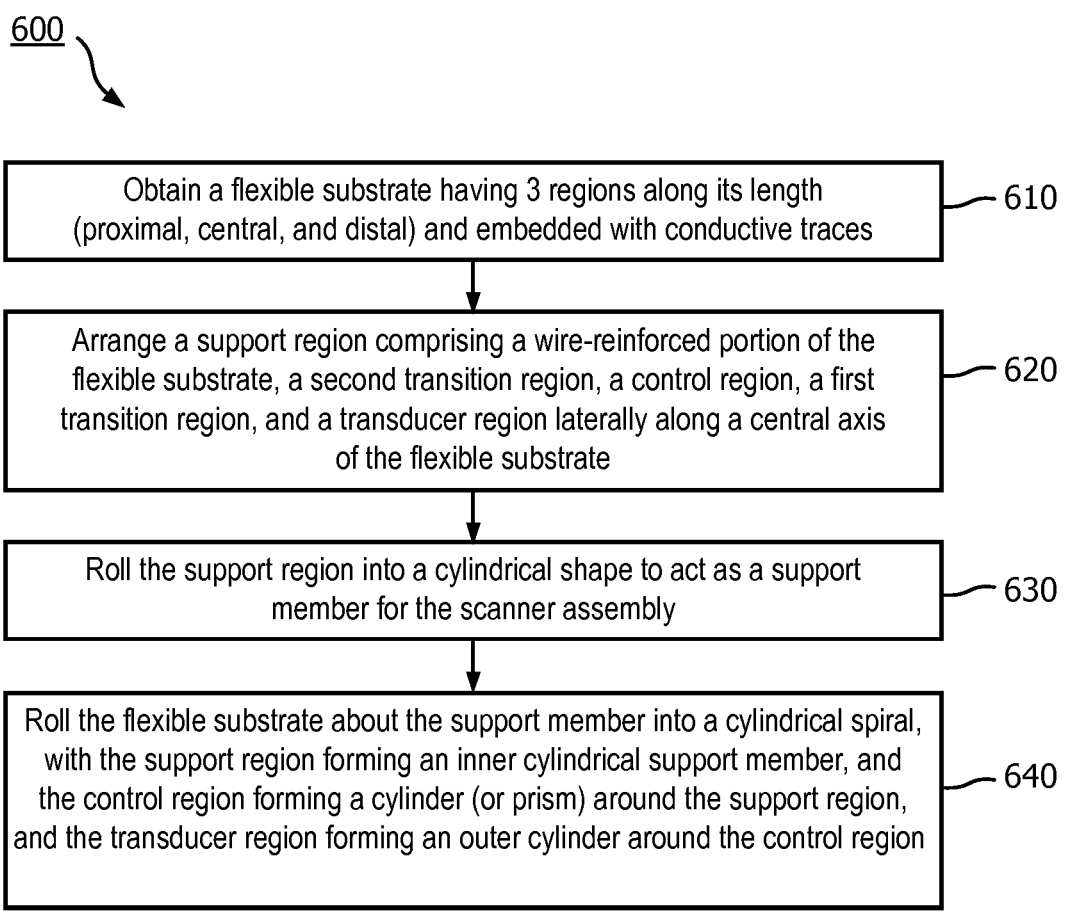
FIG. 26 is a flow diagram of a method of assembling an ultrasound imaging device according to an embodiment of the present disclosure.

FIG. 26 is a flow diagram of a method 600 of assembling an intravascular imaging device. It is understood that the steps of method 600 may be performed in a different order than shown in FIG. 26, additional steps can be provided before, during, and after the steps, and/or some of the steps described can be replaced or eliminated in other embodiments. The steps of the method 600 can be carried out by a manufacturer of the intravascular imaging device.

At step 610, the method 600 includes obtaining a flexible substrate embedded with conductive traces for coupling a transducer region to a control region. The flexible substrate may be configured to include three distinct regions extending along its length: a proximal portion, a central portion, and a distal portion.

At step 620, a support region, a second transition region, a control region, a first transition region, and a transducer region are arranged laterally along a central axis of the flexible substrate. In some embodiments, the control region, the first transition region, and the transducer region are arranged side-by-side within the central portion of the flexible substrate. The support region comprises a wire-reinforced integral portion of the flexible substrate. It may be sized and shaped so that the flexible substrate can be wrapped around it to form a generally cylindrical scanner assembly.

At step 630, the support region is rolled into a cylindrical form to act as a support member for the scanner assembly. The support region forms a support member including a lumen passing therethrough. The lumen may be sized and shaped to accommodate a guidewire or other medical instrument.

At step 640, the flexible substrate is rolled or wrapped about the support member into a cylindrical spiral, with the support region forming an inner cylindrical support member, and the control region forming a cylinder (or prism) around the support region, and the transducer region forming an outer cylinder around the control region. In this instance, the support region and the transducer region circumferentially sandwich or envelop the control region. The support region, the transducer region, and the control region remain radially spaced from one another when the scanner assembly is in the rolled configuration.

Figure 27:
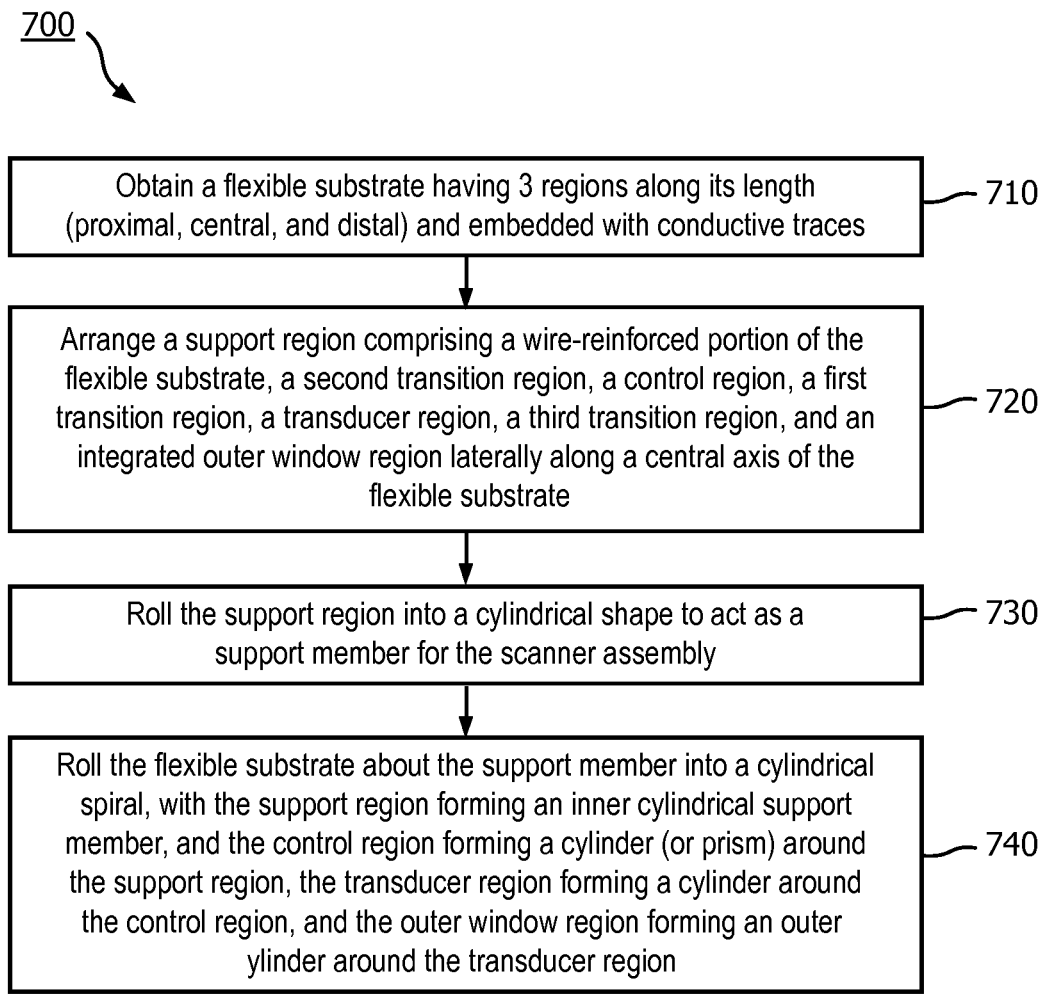
FIG. 27 is a flow diagram of a method of assembling an ultrasound imaging device according to an embodiment of the present disclosure.

FIG. 27 is a flow diagram of a method 700 of assembling an intravascular imaging device. It is understood that the steps of method 700 may be performed in a different order than shown in FIG. 27, additional steps can be provided before, during, and after the steps, and/or some of the steps described can be replaced or eliminated in other embodiments. The steps of the method 700 can be carried out by a manufacturer of the intravascular imaging device.

At step 710, the method 700 includes obtaining a flexible substrate embedded with conductive traces for coupling a transducer region to a control region. The flexible substrate may be configured to include three distinct regions extending along its length: a proximal portion, a central portion, and a distal portion.

At step 720, a support region, a second transition region, a control region, a first transition region, a transducer region, a third transition region, and an integrated outer window region are arranged laterally along a central axis of the flexible substrate. In some embodiments, the control region, the first transition region, and the transducer region are arranged side-by-side within the central portion of the flexible substrate. The support region may comprise a wire-reinforced integral portion of the flexible substrate. It may be sized and shaped so that the flexible substrate can be wrapped around it to form a generally cylindrical scanner assembly. Some embodiments lack a third transition region.

At step 730, the support region is rolled into a cylindrical form to act as a support member for the scanner assembly. The support region forms a support member including a lumen passing therethrough. The lumen may be sized and shaped to accommodate a guidewire or other medical instrument. In other embodiments, the flexible substrate lacks a support region and a second transition region. In such embodiments, the support member is formed separately from the flexible substrate, and is overlaid atop the control region prior to step 740.

At step 740, the flexible substrate is rolled or wrapped about the support member into a cylindrical spiral, with the support region forming an inner cylindrical support member, and the control region forming a cylinder (or prism) around the support region, the transducer region forming a cylinder around the control region, and the outer window region forming an outer cylinder around the transducer region. In this instance, the outer window region forms a shield circumferentially wrapped around the remainder of the flexible substrate. The window region, the support region, the transducer region, and the control region remain radially spaced from one another when the scanner assembly is in the rolled configuration.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal ultrasound imaging device comprising:
a flexible elongate member configured to be inserted into a body lumen of a patient, the flexible elongate member comprising a proximal portion and a distal portion;
an ultrasound scanner assembly disposed at the distal portion of the flexible elongate member, the ultrasound scanner assembly comprising a flexible substrate comprising a control region, a transducer region, and a window region, wherein the control region comprises a first portion of the flexible substrate to which an integrated circuit is coupled, wherein the transducer region comprises a second portion of the flexible substrate to which a transducer is coupled, and wherein the window region is a third portion of the flexible substrate to which no component is coupled,
wherein, after assembly, the flexible substrate is disposed in a rolled configuration in which the flexible substrate is rolled around itself to form an outer circumference and at least one inner circumference such that the transducer region is positioned interior to the window region, wherein the transducer region is configured to obtain ultrasound data while the transducer region is positioned interior to the window region.

2. The device of claim 1, wherein the window region comprises an integrated part of the flexible substrate.

3. The device of claim 1, wherein the rolled configuration is layered with the control region forming an inner layer, the transducer region forming a middle layer, and the window region forming an outer layer.

4. The device of claim 1, wherein the window region comprises a flange.

5. The device of claim 1, wherein, the flexible substrate comprises a plurality of nested cylinders when rolled around itself such that: a first cylinder forms the outer circumference and a second cylinder forms the inner circumference, and wherein the transducer region and the window region are located on different cylinders of the plurality of nested cylinders.

6. The device of claim 1,
wherein, in an unrolled configuration, the flexible substrate comprises a length and a width perpendicular to the length,
wherein the length of the flexible substrate extends in a direction of the length of the flexible elongate member.

7. The device of claim 6,
wherein the window region is disposed adjacent the transducer region along the width and defines an outermost edge of the flexible substrate.

8. The device of claim 6,
wherein the window region includes a variable thickness along the width from an inner window edge to an outer window edge.

9. The device of claim 8, wherein the thickness of the window region is greatest in an area radially overlying the transducer region.

10. The device of claim 6,
wherein the flexible substrate includes a central axis extending in a direction of the width, and wherein the window region, the transducer region, and the control region are disposed adjacent one another along the central axis.

11. The device of claim 10, wherein the window region, the transducer region, and the control region are coaxial along the central axis such that the window region, the transducer region, and the control region aligned with one another along the length of the flexible substrate.

12. The device of claim 6,
wherein the flexible substrate further comprises a support region,
wherein the window region, the transducer region, the control region, and the support region are disposed adjacent one another along the width.

13. The device of claim 12, the rolled configuration is layered with the support region forming an innermost first layer defining a cylindrical lumen, the control region forming a second middle layer, the transducer region forming a third middle layer, and the window region forming an outer layer.

14. The device of claim 6,
wherein the flexible substrate further comprises a transition region disposed between the window region and the transducer region along the width.

15. The device of claim 1,
wherein the outer circumference comprises the window region, and
wherein the at least one inner circumference comprises the transducer region and the control region.

16. The device of claim 1,
wherein the outer circumference comprises the window region, and
wherein the at least one inner circumference comprises the control region.

17. A method of assembling an intraluminal ultrasound imaging device, the method comprising:
obtaining a flexible substrate comprising an ultrasound transducer region, a control region, and a window region, wherein the control region comprises a first portion of the flexible substrate to which an integrated circuit is coupled, wherein the transducer region comprises a second portion of the flexible substrate to which a transducer is coupled, and wherein the window region is a third portion of the flexible substrate to which no component is coupled; and
rolling the flexible substrate around itself to form an outer circumference and at least one inner circumference such that the transducer region is positioned interior to the window region, wherein the transducer region is configured to obtain ultrasound data while the transducer region is positioned interior to the window region.

18. The method of claim 17, further comprising obtaining a support member comprising a lumen running therethrough.

19. The method of claim 18, further comprising positioning the support member adjacent the control region before rolling the flexible substrate.

20. The method of claim 19, wherein rolling the flexible substrate comprises wrapping the control region around the support member, wherein an inner layer formed by the control region surrounds the support member, a middle layer formed by the ultrasound transducer region surrounds the control region, and an outer layer formed by the window region surrounds the ultrasound transducer region.

21. The method of claim 20, wherein the window region is radially spaced from the ultrasound transducer region, the ultrasound transducer region is radially spaced from the control region, and the control region is radially spaced from the support member.

22. The method of claim 17, further comprising inserting an acoustic matching medium between the window region and the ultrasound transducer region.

* * * * *